(12) United States Patent
Jalan et al.

(10) Patent No.: US 10,639,346 B2
(45) Date of Patent: May 5, 2020

(54) TREATING HYPERAMMONEMIA, REDUCING PLASMA AMMONIA WITH TLR4 ANTAGONISTS

(71) Applicant: YAQRIT LIMITED, London (GB)

(72) Inventors: Rajiv Jalan, Chislehurst (GB); Naina Shah, Croydon (GB)

(73) Assignee: Yaqrit Limited, London (GB)

( * ) Notice: Subject to any disclaimer, the term of this patent is extended or adjusted under 35 U.S.C. 154(b) by 0 days.

(21) Appl. No.: 15/864,856

(22) Filed: Jan. 8, 2018

(65) Prior Publication Data

US 2018/0256669 A1 Sep. 13, 2018

Related U.S. Application Data

(63) Continuation of application No. 13/817,374, filed as application No. PCT/GB2011/001227 on Aug. 17, 2011, now Pat. No. 9,889,176.

(30) Foreign Application Priority Data

Aug. 17, 2010 (GB) .................................. 1013785.9

(51) Int. Cl.
A61K 38/10 (2006.01)
A61K 38/04 (2006.01)
G01N 33/68 (2006.01)

(52) U.S. Cl.
CPC .............. *A61K 38/10* (2013.01); *A61K 38/04* (2013.01); *G01N 33/6893* (2013.01); *G01N 2333/705* (2013.01); *G01N 2500/00* (2013.01); *G01N 2800/085* (2013.01); *G01N 2800/28* (2013.01); *G01N 2800/347* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,681,824 A | 10/1997 | Christ et al. ..................... | 514/53 |
| 9,889,176 B2 * | 2/2018 | Jalan ....................... | A61K 38/04 |
| 2010/0062026 A1 | 3/2010 | Modi et al. ................. | 454/248.1 |
| 2010/0168058 A1 | 7/2010 | Joosten et al. ................... | 514/54 |

OTHER PUBLICATIONS

A novel TLR4-binding peptide that inhibits LPS-induced activation of NF-kB and in vivo toxicity. European Journal of Pharmacology. vol. 594, Issues 1-3, Oct. 10, 2008, pp. 152-156. https://doi.org/10.1016/j.ejphar.2008.07.037.*
Shah et al. "TLR4 antagonist in acute liver failure: A novel therapeutic strategy." Gut, (Sep. 8, 2010) vol. 59, Supp. Suppl. 2, pp. A35, Abstract Number: P59. Meeting Info: British Association for the Study of the Liver Annual Meeting, BASL 2010. Edinburgh, United Kingdom.*
Frenhammar, et al. "Toll-Like Receptor 4 Inhibitor TAK-242 Attenuates Acute Kidney Injury in Endotoxemic Sheep". Anesthesiologv (2011): 114: 1130-7 (cited in the IDS of Jan. 8, 2018).*
Arroyo, et al."Acute-on-chronic liver failure: A new Syndrom that will re-classify cirrhosis" *Journal of Hepatology* (2015) vol. 62, pp. S131-S143.
Blasco-Algora, et al. "Acute-on-chronic liver failure: Pathogenesis, prognostic factors and management" *World J Gastroenterol* (2015) 21(42): 12125-12140.
Cunningham et al., "Role of Toll-like receptor 4 in endotoxin-induced acute renal failure," *Journal of Immunology*, (2004), 72: 2629-2635.
De Oca, et al. "Evidence of Dendritic Cell Dysfunction in Cirrhosis and Its Restoration by Toll-Like Receptor 4 Antagonism" *Hepatology* (2010) p1018A.
Frenhammar, et al. "Toll-Like Receptor 4 Inhibitor TAK-242 Attenuates Acute Kidney Injury in Endotoxemic Sheep" *Anesthesiology* (2011); 114: 1130-7.
Jalan et al. "Acute-on-Chronic Liver Failure: Pathophysiological Basis of Therapeutic Options" *Proceedings of the 6th International Conference on CRRT: Blood Purif* (2002) 20: 252-261.
K. Sugiyama, "A novel TLR4-binding peptide that inhibits LPS-induced activation of NF-KappaB and vivo toxicity," *European Journal of Pharmacology*,(2008), 594: 152-156.
Kitazawa et al., "Salvage effect of E5564, Toll-like receptor 4 antagonist on d-galactosamine and lipopolysaccharide-induced acute liver failure in rats." *Journal of Gastroenterology & Heptaology*, (2010), 25: 1009-1012.
Kitazawa et al., "Therapeutic approach to regulate innate immune response by Toll-Like receptor 4 antagonist E5564 in rats with D-galactosamine-induced acute severe liver injury," *Journal of Gastroenterology and Hepatology* (2009), 24: 1089-1094.
Leon, et al., "Discovery and Development of Toll-Like Receptor 4 (TLR4) Antagonists: A New Paradigm for Treating Sepsis and Other Diseases" *Pharmaceutical Research* (2008), vol. 25, No. 8, pp. 1751-1761.
Martin-Llahi et al., "Prognostic importance of the cause of renal failure in patiens with cirrhosis." *Gastroenterology*, (2011), 140: 488-496.
Moreau, et al., "Acute-on-Chronic Liver Failure is a Distinct Syndrome That Develops in Patients with Acute Decompensation of Cirrhosis" *Gastroenterology* (2013) 144: 1426-1437.
Opal, et al. "Effect on Eritoran, an Antagonist of MD2-TLR4, on Mortality on Patients With Severe Sepsis: The Access Randomized Trial" *JAMA* (2013) vol. 309, No. 11, pp. 1154-1162.

(Continued)

*Primary Examiner* — Maury A Audet

(74) *Attorney, Agent, or Firm* — Norton Rose Fulbright US LLP

(57) ABSTRACT

The present invention derives from the finding that increased levels of Toll like receptor 4 (TLR4) is associated with liver failure and renal dysfunction and/or brain dysfunction and that by decreasing TLR4 levels in vivo, the kidney and brain consequences of liver disease that are precipitated by superimposed infection or inflammation may be reduced. Accordingly, the invention provides TLR4 antagonists for use in a method of treating an individual suffering from liver disease presenting with renal or brain dysfunction.

12 Claims, 17 Drawing Sheets

(56) References Cited

OTHER PUBLICATIONS

Oya, et al. "Inhibition of Toll-like receptor 4 suppresses liver injury induced by biliary obstruction and subsequent intraportal lipopolysaccharide injection" *Am J Physiol Gastrointest Liver Physiol* (2014) 306: G244-G252.

Qing-Zhao Shi et al., "Betaine inhibits toll-like receptor 4 expression in rats with ethanol-induced liver injury." *World of Gastroenterology*, (2010), 16:897-903.

Rice, et al. "A randomized, double-blind, placebo-controlled trial of TAK-242 for the treatment of severe sepsis*" *Crit Care Med* (2010) vol. 38, No. 8, pp. 1685-1694.

Seki et al., "TLR4 mediates inflammation and fibrogenesis after bile duct ligation," *Hepatology*, (2005), 42: 265A-266A.

Shah, et al. "Increased renal expression and urinary excretion of TLR4 in acute kidney injury associated with cirrhosis" *Liver Int.* (2013) 33: 398-409.

Shah, et al. "Role of Toll-Like Receptor 4 in Mediating Multiorgan Dysfunction in Mice With Acetaminophen Induced Acute Liver Failure" *Liver Transplantation* (2013) 19:751-761.

UK Renal Registry, UK Renal Registry 17th annual Report: Appendix C Renal Services Described for Non-physiciands, pp. 285-288, Dec. 15, 2014, https://www.renalreg.org/wp-content/uploads/2014/12/15-App-c.pdf.

Wong et al., "Working Party Proposal for revised classification system of renal dysfunction in patients with cirrhosis," *Gut*, (2011) 60: 702-709.

International Search Report and Written Opinion dated Sep. 30, 2011, issued in International Application No. PCT/GB2011/001227.

Zager et al. "Toll-Like Receptor (TLR4) shedding and depletion: acute proximal tubular cell responses to hypoxic and toxic injury," *Am J Physiol Renal Physiol.* (2007) 292(1): F304-12.

Hennessy et al., "Targeting Toll-like receptors: emerging therapeutics?" *Nature Reviews Drug Discovery*, 2010, 9:293-307.

\* cited by examiner

A
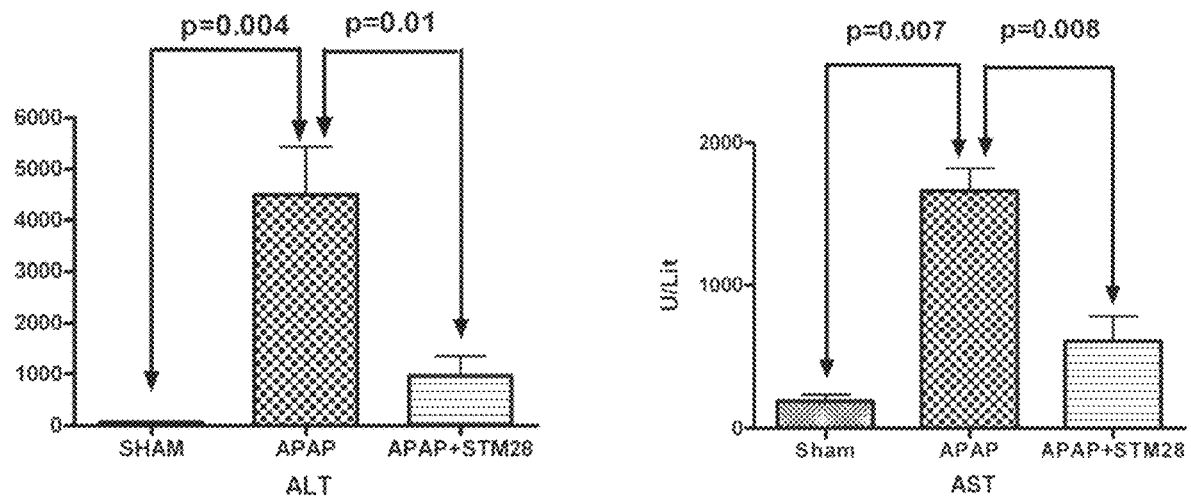
B
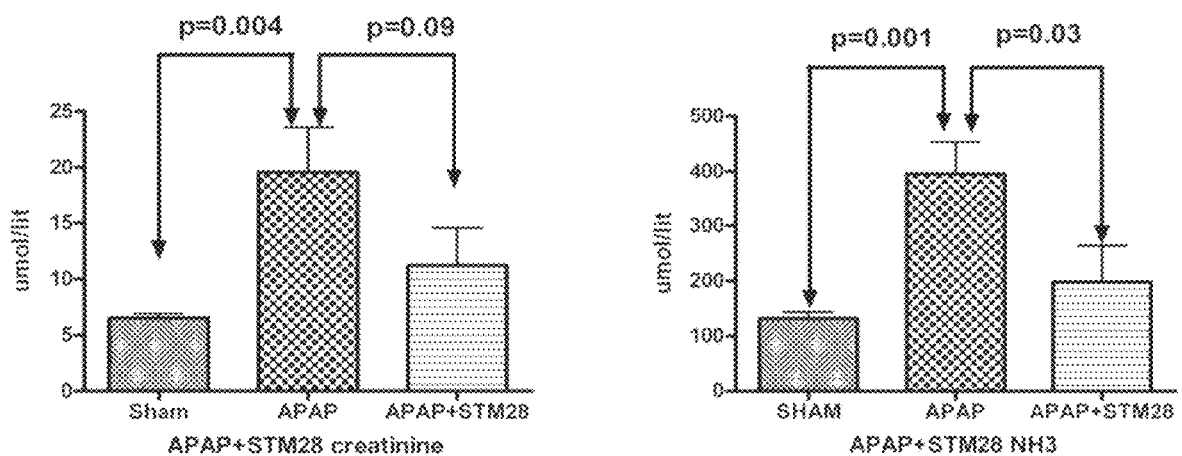
Figure 1A-B

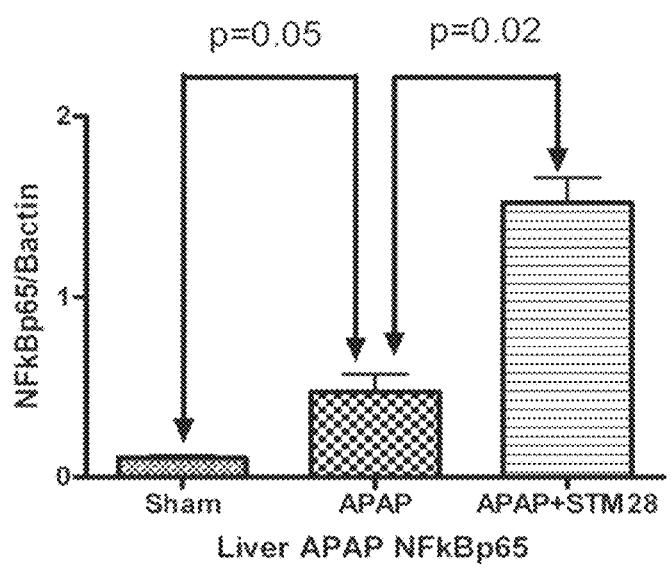
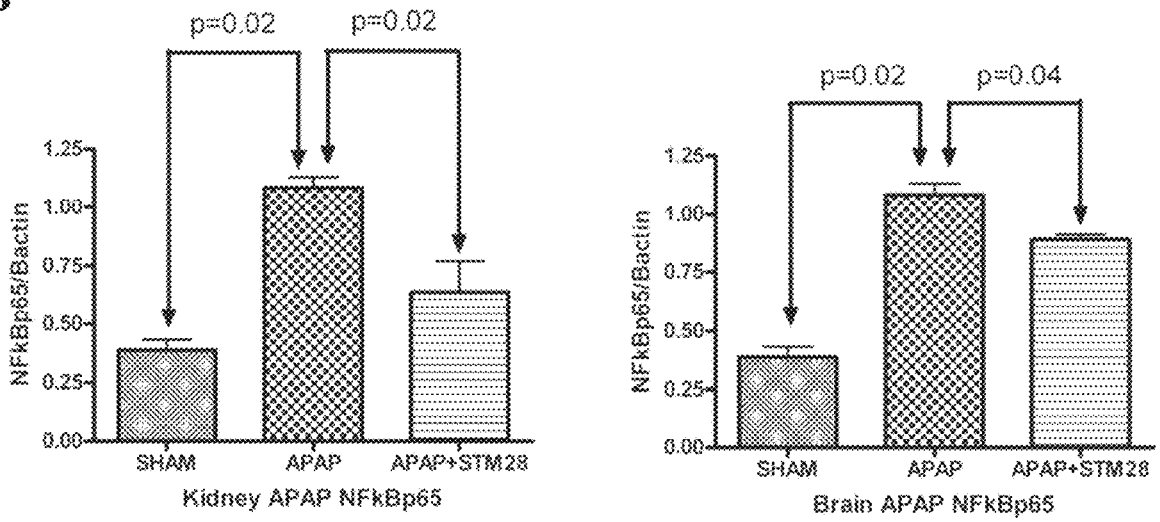
Figure 2A-B

Figure 7A-C

Kidney TLR4 densitometry
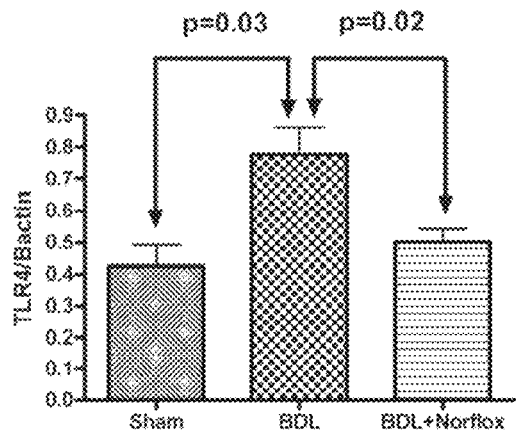 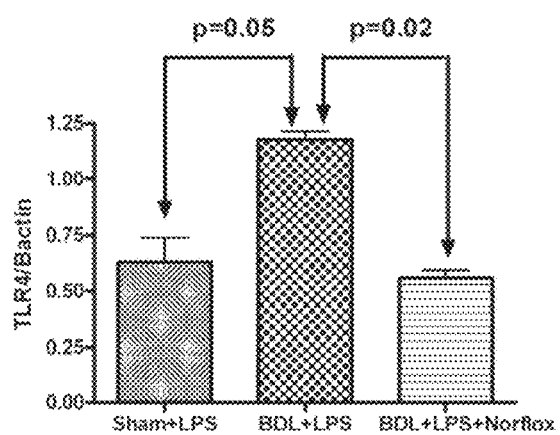
Figure 9
Kidney NFkBp65
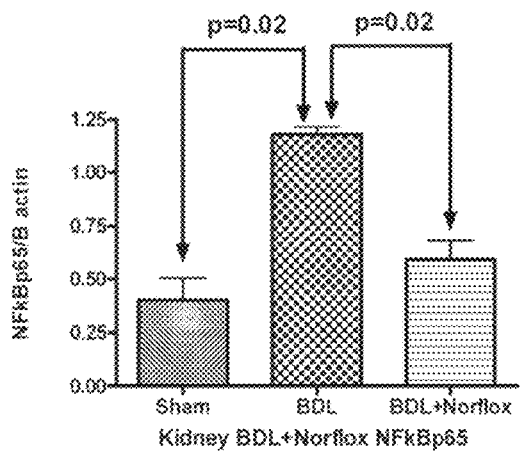 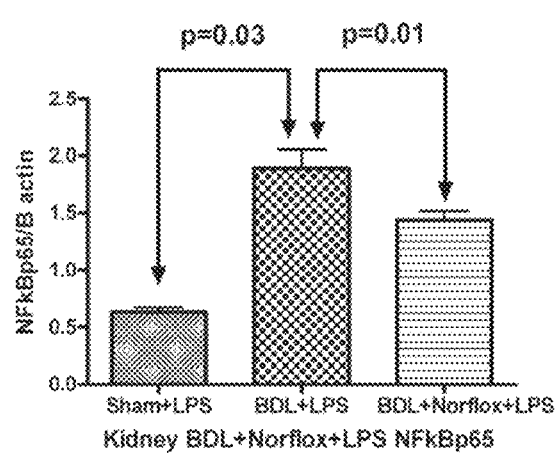
Figure 10

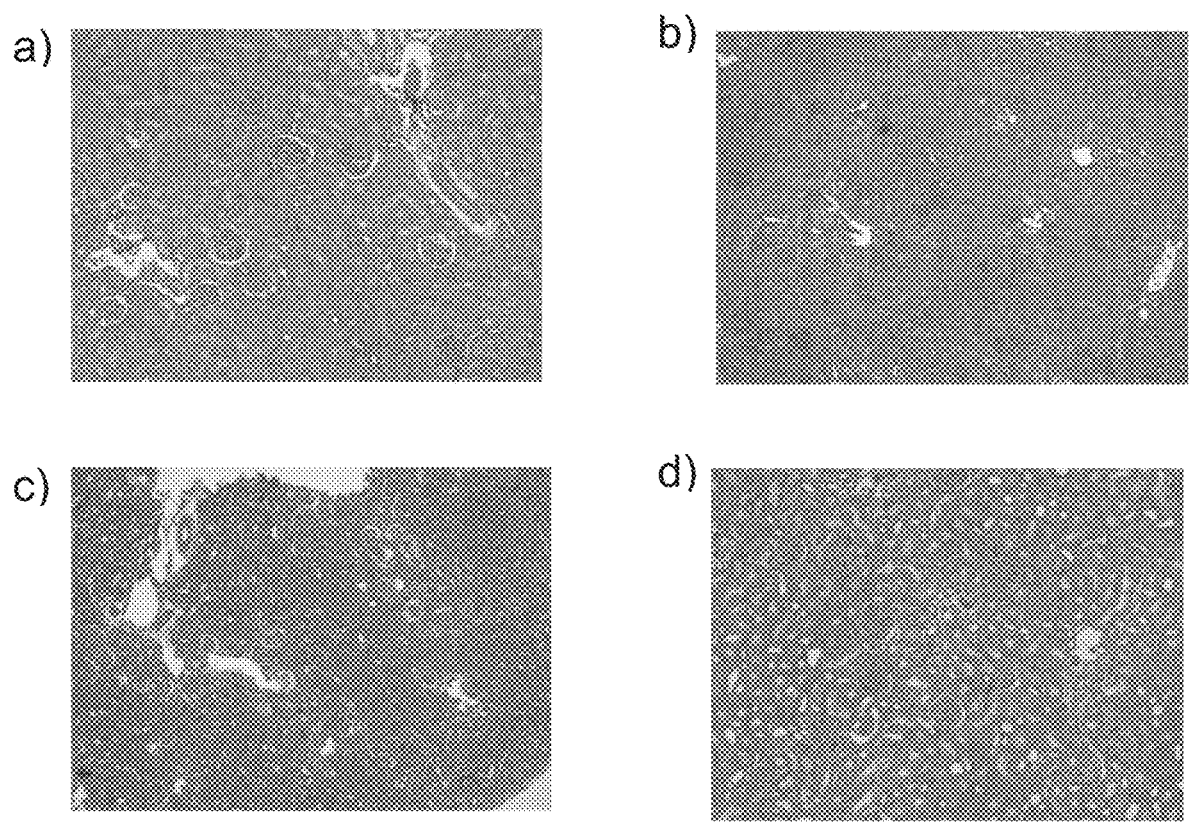
Figure 14A-D
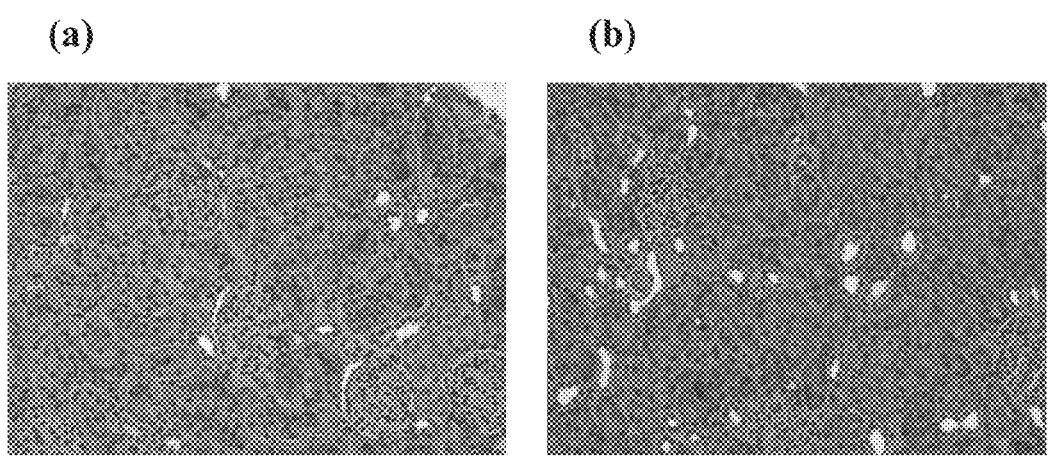
Figure 15A-B

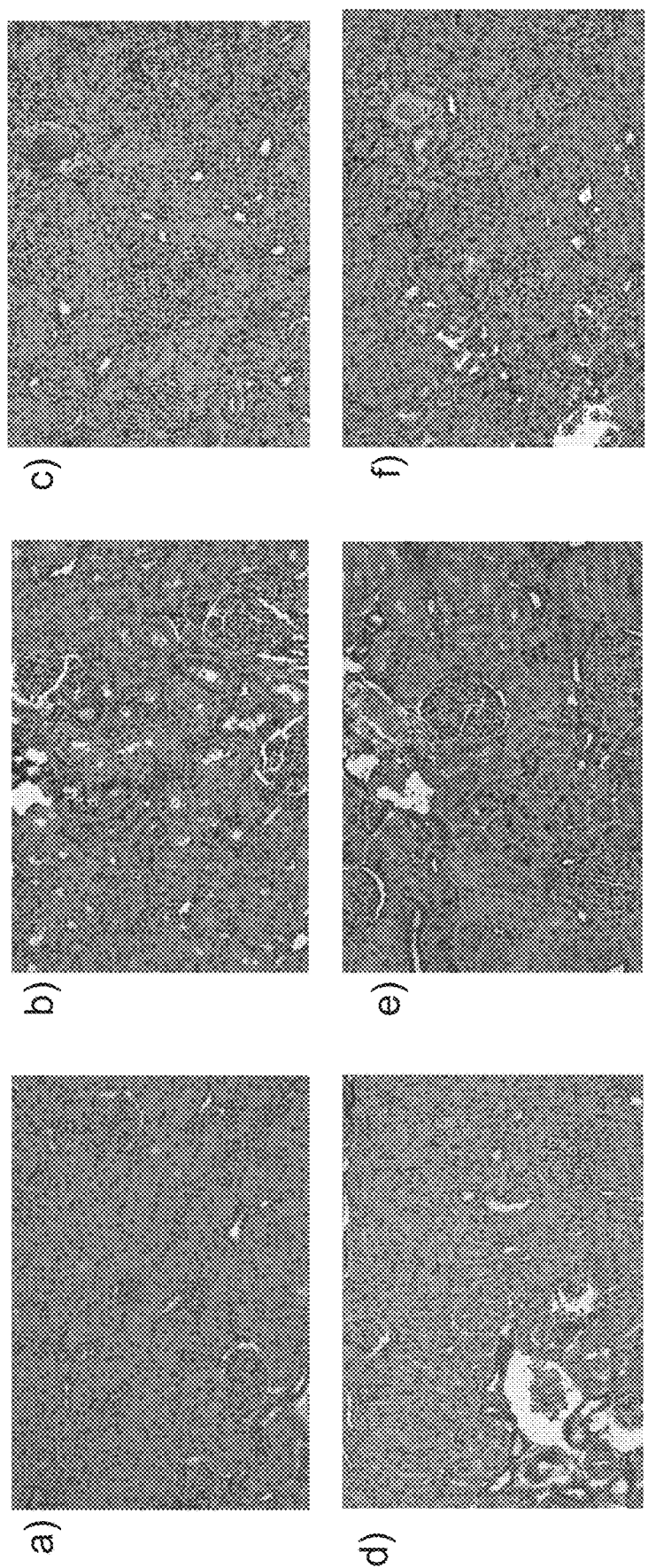
Figure 16A-F

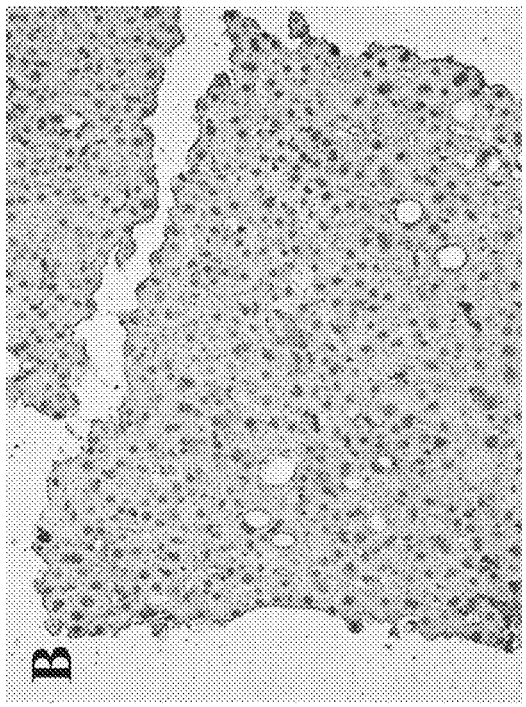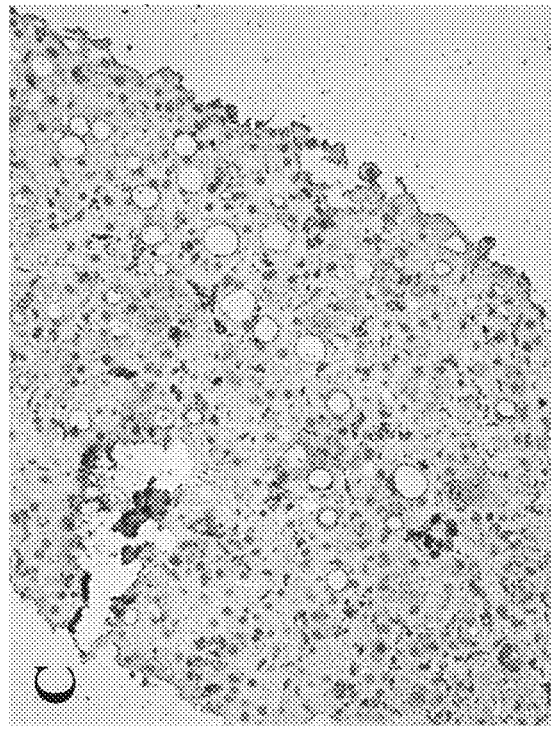
Figure 17A-C

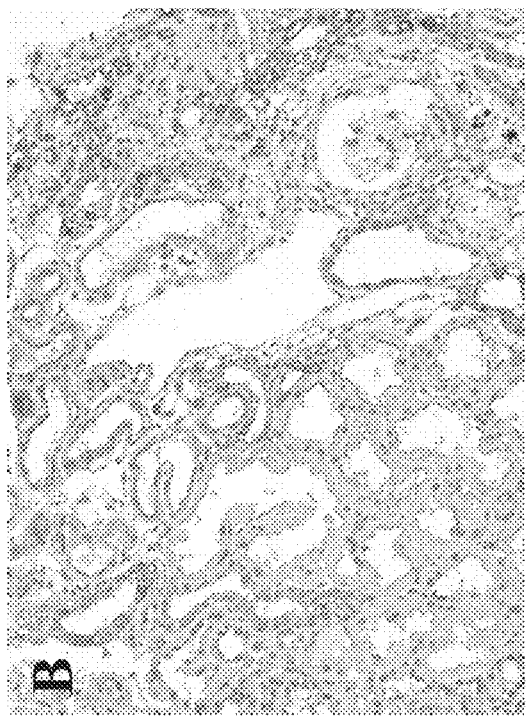
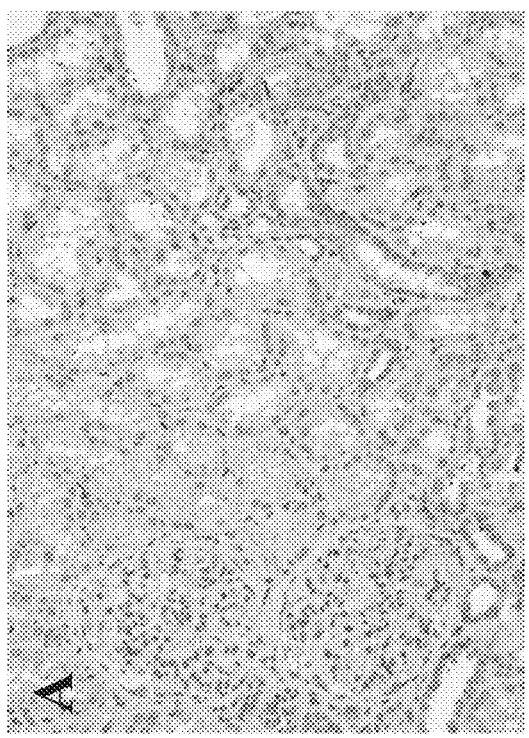
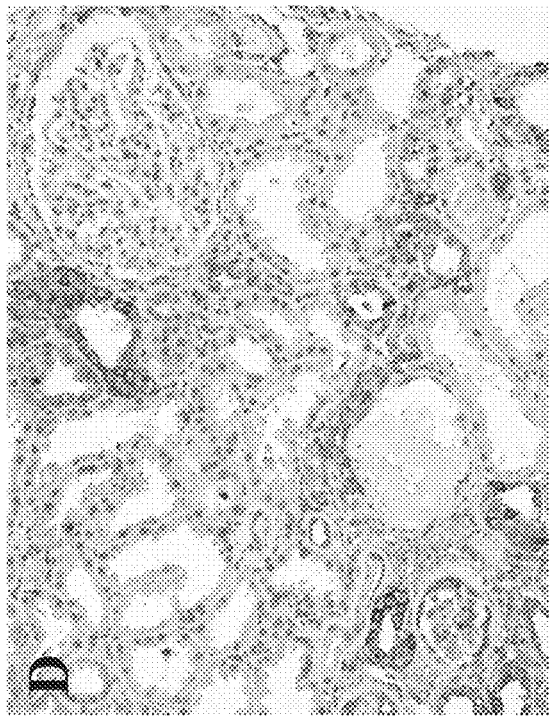
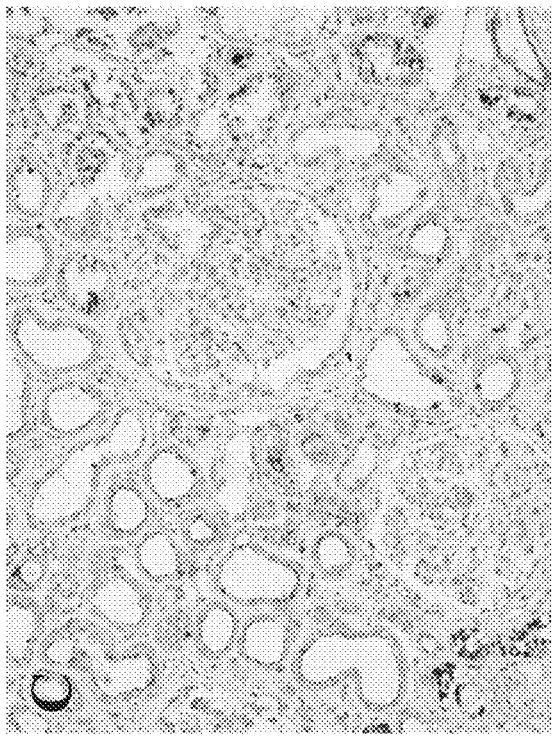
Figure 18A-D

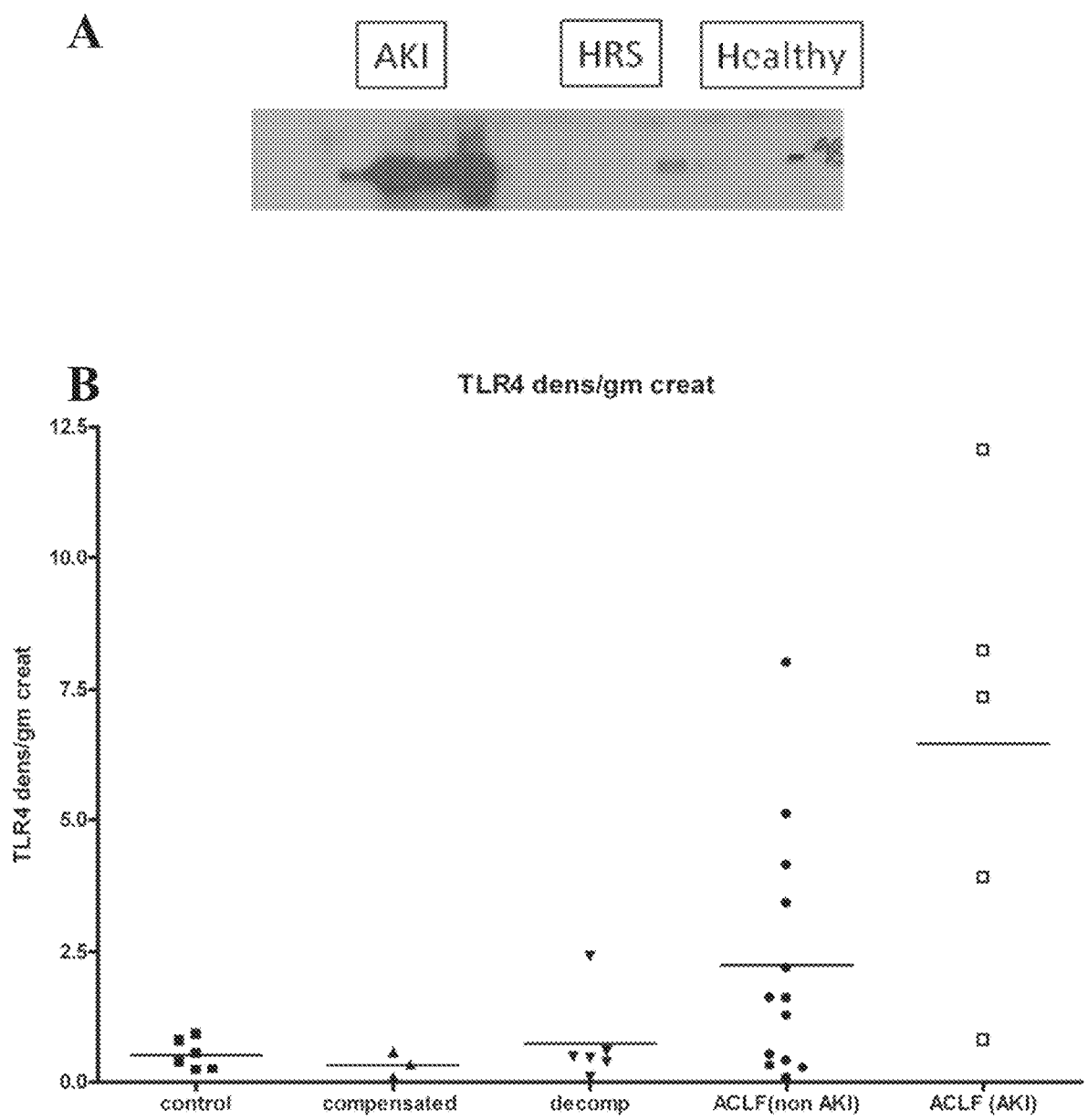
Figure 19A-B

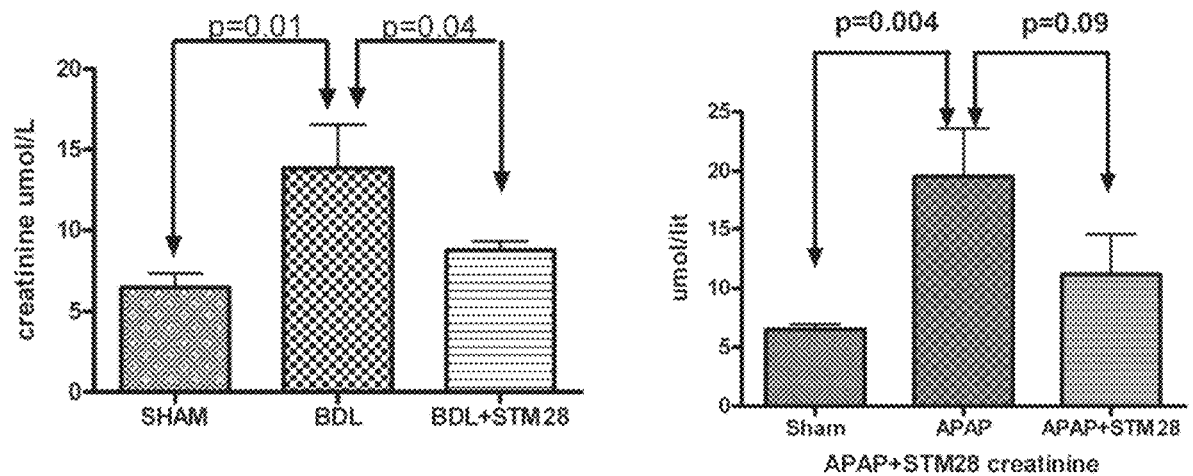
Figure 20
Figure 21
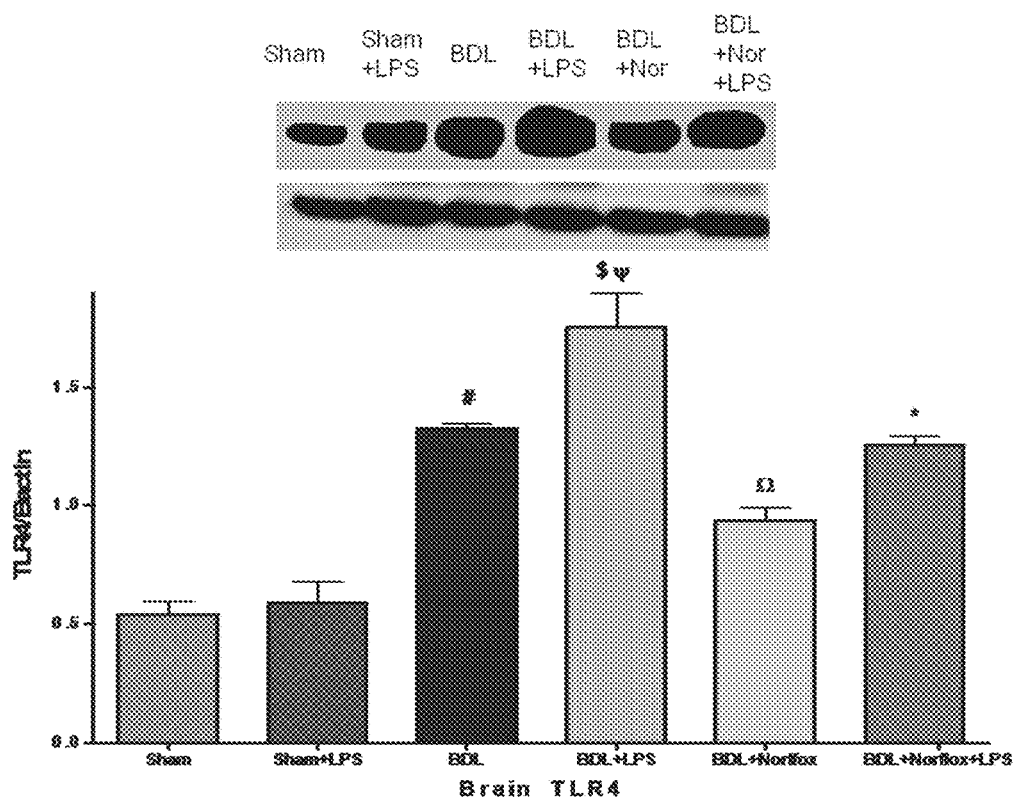
Figure 22

Figure 23A-F

Time to coma

TREATING HYPERAMMONEMIA, REDUCING PLASMA AMMONIA WITH TLR4 ANTAGONISTS

FIELD OF THE INVENTION

The present invention derives from the unexpected finding that expression of Toll like receptor (TLR4) in the kidney and brain is increased in bile duct ligated rats (a model for cirrhosis). TLR4 expression is also increased in the renal tubules of cirrhotic patients having renal failure and TLR4 levels are also increased in the urine of such patients. Furthermore, by antagonising TLR4, many of the unwanted consequences or symptoms of renal dysfunction in liver disease or liver failure may be reduced. The present invention utilises these findings to identify and provide TLR4 antagonists that may be used in the treatment or prevention of renal or brain dysfunction in liver disease, for example in the treatment of renal or brain dysfunction of cirrhosis associated with superimposed infection or inflammation.

BACKGROUND TO THE INVENTION

Renal failure and renal dysfunction are frequently presenting complications in patients with cirrhosis or liver failure and is associated with high morbidity and mortality rates. Renal failure is characterised by a rapid deterioration in kidney function and is usually fatal unless a liver transplant is performed, although various treatments, such as dialysis, can prevent advancement of the condition.

Renal dysfunction and renal failure can affect individuals with cirrhosis (regardless of cause), severe alcoholic hepatitis, or fulminant hepatic failure, and usually occurs when liver function deteriorates rapidly because of an acute injury. Renal dysfunction in cirrhosis may be due to superimposed infection and inflammation or in its absence, a situation referred to as hepatorenal syndrome (HRS). These are relatively common complications of cirrhosis, occurring in 18% of cirrhotics within one year of their diagnosis, and in 39% of cirrhotics within five years of their diagnosis.

HRS has been hypothesised to result from changes in the circulation that supplies the intestines, altering blood flow and blood vessel tone in the kidneys. The renal failure of HRS is hypothesised to be a consequence of these changes in blood flow, rather than direct damage to the kidney; the kidneys themselves appear normal to the naked eye and tissue is normal when viewed under the microscope, and the kidneys even function normally when placed in an otherwise healthy environment (such as if transplanted into a person with a healthy liver). However, the situation in patients who develop renal dysfunction in association with superimposed infection or inflammation is often associated with evidence of anatomical renal damage on histopathology.

Brain dysfunction of cirrhosis is often precipitated by infection or inflammation. Studies suggest that brain dysfunction of cirrhosis may not be completely reversible suggesting that there may be death of brain cells in this situation.

SUMMARY OF THE INVENTION

The present invention is based on the suggestion that the renal dysfunction in liver disease as described in the prior art can be divided into two separate conditions. The traditional symptoms of hepatorenal syndrome (HRS), such as changes in the circulation and reduced renal blood flow, form one condition referred to herein as HRS. However, in some patients, renal failure in liver disease is associated with superimposed infection and/or inflammation. The present invention relates to the latter group of patients in which renal dysfunction or renal failure is seen in liver disease as a result of inflammation or infection. Infection or inflammation in these patients also leads to brain dysfunction and brain swelling.

The present invention utilises antagonists of Toll like receptor 4 in the treatment and prevention of liver disease, and of symptoms and conditions that are associated with liver disease or liver failure, particularly the treatment and prevention of renal dysfunction and renal failure; and brain dysfunction and brain swelling resulting from the liver disease.

Accordingly, the invention provides an antagonist of Toll like receptor 4 (TLR4) for use in a method of treating or preventing renal dysfunction or renal failure or for treating an individual suffering from renal dysfunction and liver disease or an individual suffering from renal failure and liver disease or an individual suffering from brain dysfunction and brain swelling and liver disease. Similarly, the invention provides the use of an antagonist of TLR4 in the manufacture of a medicament for use in the treatment or prevention of renal dysfunction or renal failure or the treatment of an individual suffering from renal dysfunction and liver disease or an individual suffering from renal failure and liver disease or an individual suffering from brain dysfunction and brain swelling and liver disease. Similarly, the invention provides a method of treating or preventing renal dysfunction or renal failure or brain dysfunction and brain swelling in an individual in need thereof, particularly where the individual has liver disease such as cirrhosis, said method comprising a step of administering to said individual an antagonist of TLR4. Also the invention provides the use of an antagonist of TLR4 in the manufacture of a medicament for use in the treatment or prevention of brain dysfunction or brain swelling or the treatment of an individual suffering from brain dysfunction and liver disease or an individual suffering from renal failure and liver disease. Similarly, the invention provides a method of treating or preventing renal dysfunction or renal failure in an individual in need thereof, particularly where the individual has liver disease such as cirrhosis and superimposed infection or inflammation, said method comprising a step of administering to said individual an antagonist of TLR4.

The individual to be treated may be suffering from cirrhosis, such as alcoholic cirrhosis. The individual to be treated may be suffering from liver failure. The individual to be treated may be suffering from paracetamol overdose. The individual may be suffering from hepatorenal syndrome (HRS). The individual may be suffering from, or at risk of one or more of the following, when compared to a subject not suffering from liver disease: renal dysfunction; renal failure; HRS; brain dysfunction and brain swelling; increased plasma creatinine; increased plasma ammonia; increased liver enzyme concentrations; increased inflammation, injury or dysfunction in the liver and/or kidney and/or brain and/or blood circulation; liver tissue damage resulting from liver failure; acute liver failure, alcoholic hepatitis, and/or reperfusion injury of the liver.

In one particular embodiment, the invention provides a TLR4 antagonist as described herein for use in the treatment or prevention of renal dysfunction or renal failure; and/or brain dysfunction and brain swelling.

The antagonist for use in accordance with the invention may lead to: (a) decreased expression of TLR4 in the liver and/or kidney and/or brain of the individual; and/or (b) decreased levels of TLR4 in the liver and/or kidney and/or brain of the individual; and/or (c) decreased activity of TLR4 in the liver and/or kidney and/or brain of the individual. This would result in reduced inflammation and generation of pro-inflammatory cytokines and reduced dysfunction of organs such as the liver and/or kidneys and/or brain and/or (d) decreased levels of TLR4 in the urine of the individual.

The invention also provides a method of diagnosing renal dysfunction or renal failure or of predicting renal failure in a patient having liver disease or cirrhosis, the method comprising: (a) measuring the level of TLR4 in the urine of the patient, and (b) comparing the level of (a) with a known level of TLR4 from the urine of a control patient not suffering from liver disease or renal dysfunction, wherein an increased level in (a) compared to the control indicates that the patient has renal dysfunction or renal failure or that the patient is at increased risk of renal failure.

The invention also provides a method of identifying a patient suitable for treatment according to the present invention, the method comprising: (a) measuring the level of TLR4 in the urine of the patient, and (b) comparing the level of (a) with a known level of TLR4 from the urine of a control patient not suffering from liver disease or renal dysfunction, wherein an increased level in (a) compared to the control indicates that the patient may be suitable for treatment according to the present invention. Thus, the patient to be treated in accordance with the present invention may be a patient having an increased level of urinary TLR4 compared to the level of TLR4 in the urine or a control patient, such as a healthy patient, such as a patient not suffering from liver disease or renal dysfunction.

The invention also provides a method of identifying an agent suitable for use in treating or preventing renal dysfunction or renal failure, or brain dysfunction and brain swelling in cirrhosis or liver disease, the method comprising determining whether a test agent is capable of decreasing the amount or activity of TLR4, wherein the ability to decrease the amount or activity of TLR4 indicates that the compound may be suitable for use in treating renal dysfunction or renal failure, or brain dysfunction and brain swelling in cirrhosis or liver disease. In such a method, the amount or activity of TLR4 may be assessed in the liver and/or kidney or in tissue or cells derived from the liver and/or kidney. A screening method of the invention may comprise administering the test agent to a bile duct ligated rat and determining whether the presence of the test agent leads to a decrease in the amount or activity of TLR4 in the liver and/or kidney and/or brain of the rat.

BRIEF DESCRIPTION OF THE DRAWINGS

FIGS. 1 to 7 show the effects of treatment with acetaminophen (APAP) or APAP and the TLR4 antagonist STM28 in mice. These are compared with sham treated animals.

FIG. 1A shows the effects of such treatments on levels of the liver enzymes aspartate aminotransferase (AST) and alanine aminotransferase (ALT). FIG. 1B shows the effects of such treatments on plasma creatinine (left hand side) and ammonia (right hand side) levels.

FIG. 2 shows the effects of such treatments on levels of NFkBp65 in the liver (FIG. 2A), kidney (FIG. 2B, left hand side) and brain (FIG. 2B, right hand side).

FIGS. 3 and 4 show the effects of such treatment on levels of TNFα in the liver (FIG. 3, left hand side), kidney (FIG. 3, right hand side) and plasma (FIG. 4).

FIG. 5 shows the effects of these treatments on expression of IL1A in the liver and FIG. 6 shows the effects of these treatments on brain water.

FIG. 7 shows the histology of liver from a normal mouse (a); from mouse treated with APAP (b); and from mouse treated with APAP and STM28 (c).

FIGS. 8 to 16 show the effects of bile duct ligation (BDL) or sham operation, optionally combined with treatment with lipopolysaccharide (LPS) or norfloxacin (Norflox).

FIG. 9 shows the effects of such treatments on levels of TLR4 in the kidney, as measured by Western blotting. The effects of such treatments on the levels of NFkBp65 in the kidney (FIG. 10), TNFα (tumor necrosis factor alpha) in the kidney (FIG. 11), IL-6 (interleukin-6) in the kidney (FIG. 12), and TNFα and IL-6 in plasma (FIG. 13) are shown.

FIG. 14 shows the histology (haematoxylin & eosin) of kidney from animals that were (a) sham treated, (b) sham+LPS, (c) BDL and (d) BDL+LPS.

FIG. 15 shows the expression of TLR4 in the kidney of (a) sham+LPS animals and (b) BDL+LPS animals.

FIG. 16 shows the expression of caspase 3 in the kidney of (a) sham, (b) BDL, (c) BDL+Norflox, (d) sham+LPS, (e) BDL+LPS and (f) BDL+LPS+Norflox treated animals.

FIGS. 17 and 18 show expression of TLR4 in the liver (FIG. 17) and kidney (FIG. 18). FIG. 17: A: normal patient; B: decompensated cirrhosis; C: alcoholic hepatitis. FIG. 18: A: normal patient; B: renal impairment without infection; C: renal impairment with infection; D: alcoholic hepatitis FIG. 19 shows the levels of TLR4 in urine. A: Western Blot or urine from acute kidney injury (AKI), hepatorenal syndrome (HRS) and healthy patients. B: urinary TLR4 is greater in the patients with renal failure (AKI) and in those with ALCF (cirrhosis associated with superimposed infection or inflammation) compared with those patients that had hepatorenal syndrome (decomp). Control=healthy patients, Compensated=compensated cirrhosis patients.

FIG. 20 shows creatinine levels in mice. SHAM=sham treated (control) mice; BDL=bile duct ligated mice; STM28=mice treated with the TLR4 antagonist STM28.

FIG. 21 shows creatinine levels in mice. Sham=control mice. APAP=mice treated with paracetamol. STM28=mice treated with the TLR4 antagonist STM28.

FIGS. 22 to 25 show measurements in the brain from bile duct ligated (BDL) rats, Sham (normal) rats and rats treated with lipopolysaccharide (LPS) and/or Norfloxacin (Norflox). FIG. 22 shows brain TLR4 protein expression, FIG. 23 shows brain TLR4 immunohistochemistry in A: sham treated, B: BDL,C: BDL+Norfloxacin, D: sham+LPS, E: BDL+LPS, F: BDL+Norfloxacin+LPS.

FIG. 24 shows brain water levels and FIG. 25 shoes the effect of norfloxacin (norflox) and LPS on survival of BDL rats.

DETAILED DESCRIPTION OF THE INVENTION

Figure 3:
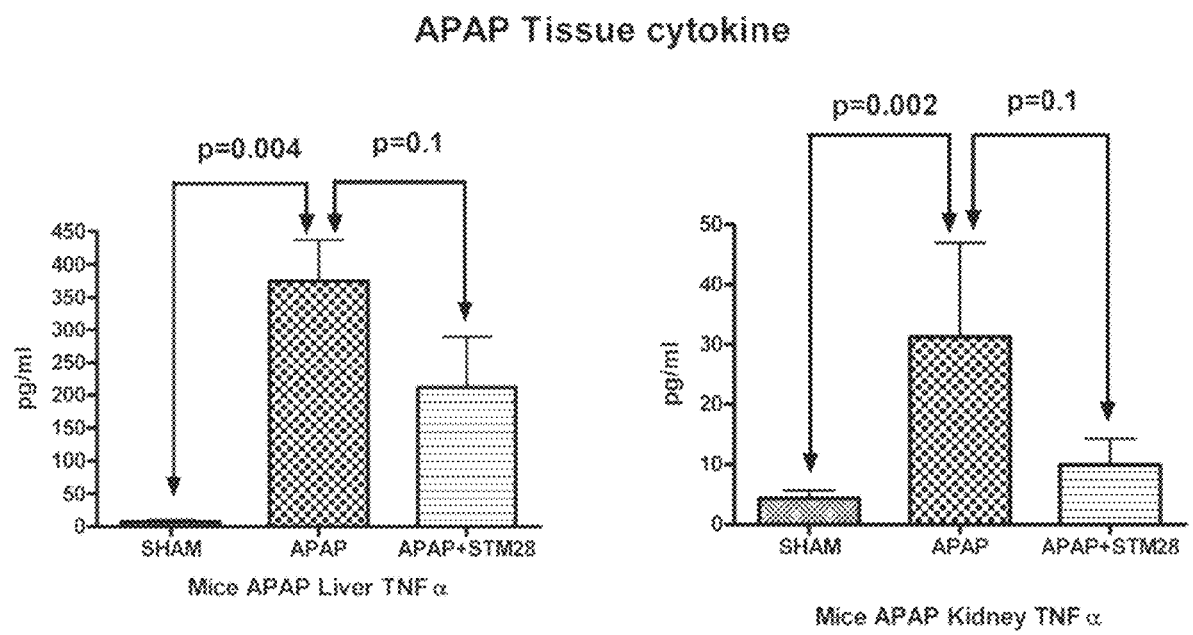

The inventors have unexpectedly found that Toll-like receptor 4 (TLR4) expression is altered in liver disease and symptoms and conditions associated with liver disease. In particular, expression of TLR4 is associated with renal dysfunction in liver disease and associated with the likelihood of renal failure in liver disease.

The Toll-like receptors (TLRs) are a class of proteins that play a key role in the innate immune system. They are single, membrane-spanning, non-catalytic receptors that recognize structurally conserved molecules derived from microbes. Once these microbes have breached physical barriers such as the skin or intestinal tract mucosa, they are recognized by TLRs which activate immune cell responses.

Toll-like receptor 4 is a protein that in humans is encoded by the TLR4 gene. TLR 4 detects lipopolysaccharide on Gram-negative bacteria and is thus important in the activation of the innate immune system. TLR4 has also been designated as CD284 (cluster of differentiation 284).

The inventors have investigated the expression of TLR4 in tissues and organs of animals suffering from liver disease or liver failure. They have further investigated the effects of inhibiting TLR4 in such animals.

As described in the Examples, the inventors have found that TLR4 appears to play a role in the pathogenesis of multiorgan failure in liver failure such as ALF. Administration of a TLR4 antagonist in a model of ALF led to a reduction in a number of the key symptoms associated with liver failure, including a reduction in the levels of liver enzymes, plasma ammonia, brain water, decreased expression of inflammatory mediators in key organs such as the kidneys and brain, and improved renal function. This suggests that TLR4 may play a key role in mediating the effects of liver failure and that by antagonising or inhibiting TLR4 in a patient in need thereof, these effects may be reduced.

The inventors have also found that TLR4 may play a particular role in the kidney and the brain.

It had previously been thought that the kidneys were normal in hepatorenal syndrome (HRS) and that HRS was caused by hemodynamic factors caused by the liver disease, rather than any defect in the kidneys themselves. The inventors have unexpectedly found that expression of TLR4 is increased in the kidney in a model of cirrhosis and is further increased in a model of cirrhosis with increased inflammation. TLR4 expression is decreased in such models if, for example, gut bacteria are removed by antibiotic treatment. The inventors therefore propose that a number of patients previously diagnosed with HRS are in fact suffering from renal dysfunction which is associated with inflammation or infection.

In cirrhosis, brain dysfunction was thought to be related primarily to the neurotoxic effects of ammonia. The inventors have found that the expression of the Toll-like receptor 4 is upregulated in the brain in a rodent model of cirrhosis. The inventors therefore propose that a number of patients previously diagnosed with ammonia related brain dysfunction are in fact suffering from brain dysfunction which is associated with inflammation or infection that is mediated through the toll like receptor 4.

The present invention thus derives from the inventors' findings of the role of TLR4 in liver disease, particularly in patients suffering from renal dysfunction, brain dysfunction and brain swelling. The present invention utilises these effects by proposing antagonists of TLR4 as therapeutic agents for use in the treatment or prevention of such conditions.

TLR4 Antagonists

The present invention relates to the antagonism of Toll like receptor 4 (TLR4). An antagonist of TLR4 may be any compound or molecule that inhibits or decreases the activity, function or amount of TLR4. Preferably the antagonist functions in the liver and/or kidney and/or brain of the patient with liver failure. The antagonist may act preferentially in the liver and/or kidney or may act at a number of locations including the liver and/or kidney and/or brain. Preferably the antagonist leads to a decrease in TLR4 activity, function or amount in the organs of an individual to whom the antagonist is administered, such as in one or more of the liver, kidneys, brain, and the heart of the individual. The antagonist may be targeted to the liver, kidney or other organs such as those listed above during administration as discussed further below.

Preferred antagonists are those that decrease the activity or amount of TLR4 by at least 10%, at least 20%, at least 30%, at least 40%, at least 50%, at least 60%, at least 70%, at least 80% or at least 90% compared to the amount seen in the absence of the antagonist. For example, decreases of these sizes may be seen in the liver or liver tissue of a subject to whom the agonist has been administered. Decreases of these sizes may be seen in other tissues or organs of the individual, such as in the kidney and/or heart of the individual.

An antagonist of TLR4 may reduce the activity or amount of TLR4 to an amount or activity that is the same, similar to, or equivalent to, that seen in an individual not suffering from liver disease. For example, as explained herein, the expression of TLR4 is found to be increased in association with a model of cirrhosis. Use of an TLR4 antagonist in accordance with the present invention may lead to a reduction in TLR4 expression in the liver and/or kidneys and/or brain of the individual being treated to a normal level, such as a level that would be seen or would be expected in an individual not suffering from chronic liver disease or cirrhosis.

The antagonist may act specifically to antagonise TLR4. That is, the effect of the antagonist on TLR4 may be greater than any other biological effect of the antagonist. Such an antagonist may be specific to the inhibition of TLR4, that is it may decrease the activity of TLR4, but not other receptors such as other Toll like receptors. Such an antagonist may additionally or alternatively be specific to the expression of TLR4, that is it may decrease the expression of TLR4 but not other receptors such as other Toll like receptors. An antagonist for use in accordance with the present invention may be an antagonist of TLR4 as described herein, that does not act as an antagonist of other Toll like receptors. An antagonist for use in accordance with the present invention may act on TLR4 in preference to other Toll like receptors. For example, an antagonist of TLR4 for use in accordance with the present invention may have one or more of the characteristics of an TLR4 antagonist as described herein, but may not have such characteristics in relation to other Toll like receptors, or may have such characteristics to a lower level in relation to other Toll like receptors when compared to TLR4. For example, an antagonist that decreases the activity of TLR4 may not decrease the activity of other Toll like receptors, or may decrease the activity of other Toll like receptors to a lesser extent, such as a lower percentage decrease, than its effect on TLR4. An antagonist that decreases the expression or amount of TLR4 may not decrease the expression or amount of other Toll like receptors, or may decrease the expression of other Toll like receptors to a lesser extent, such as a lower percentage decrease, than its effect on TLR4. An TLR4 antagonist as described herein may have an effect on other Toll like receptors, such as antagonism of the activity, signalling or expression of one or more other Toll like receptors, that is less than 25%, less than 20%, less than 15%, less than 10%, less than 5%, less than 1%, or less than 0.1% the effect of that antagonist on the activity, signalling or expression of TLR4.

By other Toll like receptors herein is meant any Toll like receptor that is not TLR4. At least 13 groups of Toll like receptor have been identified in mammals. The other Toll like receptor may be any such Toll like receptor that is not TLR4. The other Toll like receptor may be one or more of these Toll like receptors. The other Toll like receptor may be all other Toll like receptors that are not TLR4.

The specificity of the TLR4 antagonist may apply within the whole body of the individual to be treated, that is the actions of the TLR4 antagonist may be specific as discussed above throughout the body of the individual. The specificity of the TLR4 antagonist may apply within particular tissues of the individual, such as the liver, kidneys and/or heart and/or brain. That is, in one embodiment, the TLR4 antagonist may act specifically to antagonise TLR4 as discussed above within the liver and/or kidney and/or other organs of the individual being treated.

The TLR4 antagonist may therefore be a specific antagonist of TLR4 as described above. For example, the TLR4 antagonist may not be an antagonist of other Toll like receptors, or may have no significant effect on the activity or expression of other Toll like receptors.

Any agent capable of inhibiting the activity or function of TLR4 may be suitable for use in the methods of the present invention. Antagonists for use in accordance with the present invention may be direct or indirect antagonists of TLR4.

Direct antagonists are agents whose activity is directly on TLR4. For example, direct antagonists may be agents that act directly on the TLR4 receptor to decrease its activity. A direct antagonist may be an agent that disrupts TLR4 function or that destabilises the TLR4 receptor. A direct antagonist may decrease the amount of TLR4 by destroying or disrupting TLR4 molecules within the patient. A direct antagonist may be an agent that acts on the TLR4 gene, promoter or other gene regulatory regions to decrease expression of the TLR4. A direct antagonist may decrease expression of TLR4 by preventing or reducing expression from the endogenous TLR4 gene.

A TLR4 antagonist may act to disrupt the activity of TLR4. For example, the antagonist may act by preventing activation of TLR4 or y preventing formation of functional complexes comprising TLR4.

Any agent or molecule having the properties described above may be used as an TLR4 antagonist in accordance with the present invention. The test agent may be, or may comprise, for example, a peptide, polypeptide, protein, antibody, polynucleotide, small molecule or other compound that may be designed through rational drug design starting from known antagonists of TLR4.

Examples of TLR4 antagonists or inhibitors that may be used in accordance with the present invention include:

The peptide STM28 as described in Sugiyama et al (European Journal of Pharmacology 594 (2008) 152-156);

Ethyl (6R)-6-[N-(2-chloro-4-fluorophenyl)sulfamoyl]cyclohex-1-ene-1-carboxylate (TAK-242) which acts by blocking the signaling mediated by the intracellular domain of TLR4, but not the extracellular domain;

Tetrasodium [(2R,3R,4R,5S,6R)-4-decoxy-5-hydroxy-6-[[(2R,3R,4R,5S,6R)-4-[(3R)-3-methoxydecoxy]-6-(methoxymethyl)-3-[[(Z)-octadec-11-enoyl]amino]-5-phosphonatooxyoxan-2-yl]oxymethyl]-3-(3-oxotetradecanoylamino)oxan-2-yl] phosphate (eritoran), which may be provided as E5564. E5564 contains eritoran tetrasodium as an active ingredient. E5564 blocks receptor signal transduction and inhibits the release of the inflammatory cytokines IL-1 and TNF.

NI-0101 is an anti-TLR4 monoclonal antibody that binds to an epitope on TLR4 which interferes with its dimerisation required for intracellular signalling and induction of pro-inflammatory pathways. NI-0101 is a product of Novlmmune SA.

OxPAPC (1-palmitoyl-2-arachidonyl-sn-glycero-3-phosphorylcholine), which is an oxidized phospholipid that has been shown to inhibit the signaling induced by bacterial lipopeptide and lipopolysaccharide (LPS).

IAXO compounds such as IAXO-101 (Methyl 6-deoxy-6-N-dimethyl-N-cyclopentylammonium-2, 3-di-O-tetradecyl-α-D-glucopyranoside iodide), IAXO-102 Methyl 6-Deoxy-6-amino-2,3-di-O-tetradecyl-α-D-glucopyranoside, or IAXO-103 (N-(3,4-Bis-tetradecyloxy-benzyl)-N-cyclopentyl-N,N-dimethylammonium iodide)

Compounds that target TLRs such as TLR4 are reviewed in Hennessy et al (2010) Nature Reviews Drug Discovery 9: 293-307.

Preferably the TLR4 antagonist is not LPS.

The TLR4 antagonist may be a molecule that is capable of binding to and preventing or disrupting the activity of TLR4.

Accordingly, one group of TLR4 antagonists for use in accordance with this invention are anti-TLR4 antibodies. Such an antibody may be monoclonal or polyclonal or may be an antigen-binding fragment thereof. For example, an antigen-binding fragment may be or comprise a F(ab)2, Fab or Fv fragment, i.e. a fragment of the "variable" region of the antibody, which comprises the antigen binding site. An antibody or fragment thereof may be a single chain antibody, a chimeric antibody, a CDR grafted antibody or a humanised antibody.

An antibody may be directed to the TLR4 molecule, i.e. it may bind to epitopes present on TLR4 and thus bind selectively and/or specifically to TLR4. An antibody may be directed to another molecule that is involved in the expression and/or activity of TLR4. For example, a polyclonal antibody may be produced which has a broad spectrum effect against one or more epitopes on TLR4 and/or one or more other molecules that are involved in the expression and/or activity of TLR4.

Antibodies can be produced by any suitable method. Means for preparing and characterising antibodies are well known in the art, see for example Harlow and Lane (1988) "Antibodies: A Laboratory Manual", Cold Spring Harbor Laboratory Press, Cold Spring Harbor, N.Y. For example, an antibody may be produced by raising antibody in a host animal against the whole polypeptide or a fragment thereof, for example an antigenic epitope thereof, herein after the "immunogen".

An antibody, or other compound, "specifically binds" to a molecule when it binds with preferential or high affinity to the molecule for which it is specific but does substantially bind not bind or binds with only low affinity to other molecules. A variety of protocols for competitive binding or immunoradiometric assays to determine the specific binding capability of an antibody are well known in the art (see for example Maddox et al, J. Exp. Med. 158, 1211-1226, 1993). Such immunoassays typically involve the formation of complexes between the specific protein and its antibody and the measurement of complex formation.

The TLR4 antagonist may be an antisense oligonucleotide, such as an antisense oligonucleotide against the gene encoding a TLR4 protein. The term "antisense oligonucleotide" as used herein means a nucleotide sequence that is complementary to the mRNA for a desired gene. Such an antisense oligonucleotide may selectively hybridise with the desired gene. In the context of the present invention, the desired gene may be the gene encoding TLR4.

The TLR4 antagonist may modulate expression of the TLR4 gene. For example, the TLR4 antagonist may be a short interfering nucleic acid (siRNA) molecule, double stranded RNA (dsRNA), micro RNA, deoxyribose nucleic acid interference (DNAi) or short hairpin RNA (shRNA) molecule.

The term "selectively hybridise" as used herein refers to the ability of a nucleic acid to bind detectably and specifically to a second nucleic acid. Oligonucleotides selectively hybridise to target nucleic acid strands under hybridisation and wash conditions that minimise appreciable amounts of detectable binding to non-specific nucleic acids. High stringency conditions can be used to achieve selective hybridisation conditions as known in the art. Typically, hybridisation and washing conditions are performed at high stringency according to conventional hybridisation procedures. Washing conditions are typically 1-3×SSC, 0.1-1% SDS, 50-70° C. with a change of wash solution after about 5-30 minutes.

The TLR4 antagonist may be a nucleic acid molecule such as an antisense molecule or an aptamer. The nucleic acid molecule may bind a specific target molecule.

Aptamers can be engineered completely in vitro, are readily produced by chemical synthesis, possess desirable storage properties, and elicit little or no immunogenicity in therapeutic applications. These characteristics make them particularly useful in pharmaceutical and therapeutic utilities.

The terms "nucleic acid molecule" and "polynucleotide" are used interchangeably herein and refer to a polymeric form of nucleotides of any length, either deoxyribonucleotides or ribonucleotides, or analogs thereof. A nucleic acid may comprise conventional bases, sugar residues and internucleotide linkages, but may also comprise modified bases, modified sugar residues or modified linkages. A nucleic acid molecule may be single stranded or double stranded.

In general, aptamers may comprise oligonucleotides that are at least 5, at least 10 or at least 15 nucleotides in length. Aptamers may comprise sequences that are up to 40, up to 60 or up to 100 or more nucleotides in length. For example, aptamers may be from 5 to 100 nucleotides, from 10 to 40 nucleotides, or from 15 to 40 nucleotides in length. Where possible, aptamers of shorter length are preferred as these will often lead to less interference by other molecules or materials.

Aptamers may be generated using routine methods such as the Systematic Evolution of Ligands by EXonential enrichment (SELEX) procedure. SELEX is a method for the in vitro evolution of nucleic acid molecules with highly specific binding to target molecules. It is described in, for example, U.S. Pat. Nos. 5,654,151, 5,503,978, 5,567,588 and WO 96/38579. The SELEX method involves the selection of nucleic acid aptamers and in particular single stranded nucleic acids capable of binding to a desired target, from a collection of oligonucleotides. A collection of single-stranded nucleic acids (e.g., DNA, RNA, or variants thereof) is contacted with a target, under conditions favourable for binding, those nucleic acids which are bound to targets in the mixture are separated from those which do not bind, the nucleic acid-target complexes are dissociated, those nucleic acids which had bound to the target are amplified to yield a collection or library which is enriched in nucleic acids having the desired binding activity, and then this series of steps is repeated as necessary to produce a library of nucleic acids (aptamers) having specific binding affinity for the relevant target.

Any of the antagonists described herein may therefore be used to antagonise TLR4, i.e. to decrease the amount of TLR4 that is present, and/or the activity or the function of the TLR4. Preferably these antagonising effects take place in the liver and/or kidney and/or brain.

An antagonist of TLR4 may be an agent that decreases the production of endogenous TLR4. For example, the agent may act within the cells of the subject to inhibit or prevent the expression of TLR4. Such an agent may be a transcription factor or enhancer that acts on the TLR4 gene to inhibit or prevent gene expression.

Preferably the antagonist of TLR4 is an agent capable of reducing injury and/or organ dysfunction caused by administration of a hepatotoxin, such as acetaminophen. For example, this ability may be tested in a suitable animal model, such as a non-human animal (e.g. a mouse or rat), that is treated with such a hepatotoxin. The effects of the potential TLR4 antagonist on such an animal may be assessed. The TLR4 antagonist may be administered prior to, at the same time as, or after, administration of the hepatotoxin to the animal. The effects of the hepatotoxin in the presence of the antagonist may be compared to the effects of the hepatotoxin in the absence of the TLR4 antagonist, for example in a vehicle-treated animal. A suitable TLR4 antagonist for use in accordance with the present invention may reduce injury or organ dysfunction in the animal compared to that seen in the absence of the TLR4 antagonist. This reduced injury or dysfunction may be characterised using any of the criteria discussed further herein, such as a reduction in liver enzymes, a reduction in plasma creatinine and/or ammonia levels, an alteration in inflammatory modulator levels such as levels of NFκB or TNFα, a reduction in the level of interleukin 1a in the liver, a decrease in brain water, a decrease in tissue damage in the organ, or other characteristics of injury or organ dysfunction that would be expected to result from treatment with a hepatotoxin. The organ may be, for example, the liver, the kidney, the heart and/or the brain. A suitable TLR4 antagonist would be expected to have such improved effects compared with the effects that are seen with administration the hepatotoxin in the absence of the TLR4 antagonist.

Screening Methods

The present invention also provides methods for the identification of agents suitable for use in the treatment or prevention of liver disease or of renal dysfunction or renal failure, or brain dysfunction and brain swelling, associated with liver disease. For example, the invention provides methods for the identification of antagonists of TLR4 which are suitable for use in treating liver disease, such as in treating or preventing renal dysfunction or renal failure associated with liver disease or brain dysfunction and brain swelling associated with liver disease. Antagonists identified by this method may be antagonists of TLR4 having any of the characteristics or effects described above. Antagonists identified by the methods described herein may be suitable for use in the treatment or prevention of liver disease or in the treatment or prevention of any of the conditions or symptoms described herein, such as renal dysfunction or renal failure associated with liver disease or brain dysfunction and brain swelling associated with liver disease.

Accordingly, the invention provides a method of identifying an agent for use in the treatment or prevention of renal dysfunction or renal failure associated with liver disease or brain dysfunction and brain swelling associated with liver disease, the method comprising determining whether a test agent is capable of decreasing the activity or expression of TLR4. For example, the method may involve determining whether a test agent is capable of decreasing the amount or activity of TLR4, wherein the ability to decrease the amount or activity of TLR4 indicates that the compound may be suitable for use in treating or preventing renal dysfunction or renal failure associated with liver disease or brain dysfunction and brain swelling associated with liver disease as described herein.

A test agent for use in a screening method of the invention refers to any compound, molecule or agent that may potentially antagonise TLR4. The test agent may be, or may comprise, for example, a peptide, polypeptide, protein, antibody, polynucleotide, small molecule or other compound that may be designed through rational drug design starting from known antagonists of TLR4.

The test agent may be any agent having one or more characteristics of an antagonist of TLR4 as described above.

The test agent to be screened could be derived or synthesised from chemical compositions or man-made compounds. Candidate agents may be obtained from a wide variety of sources including libraries of synthetic or natural compounds. Suitable test agents which can be tested in the above assays include compounds derived from combinatorial libraries, small molecule libraries and natural product libraries, such as display (e.g. phage display) libraries. Multiple test agents may be screened using a method of the invention in order to identify one or more agents having a suitable effect on TLR4, such as inhibition of TLR4 activity or expression.

The screening methods of the invention may be carried out in vivo, ex vivo or in vitro. In particular, the step of contacting a test agent with TLR4 or with a cell or tissue that comprises TLR4 may be carried out in vivo, ex vivo or in vitro. The screening methods of the invention may be carried out in a cell-based or a cell-free system. For example, the screening method of the invention may comprise a step of contacting a cell or tissue comprising TLR4 with a test agent and determining whether the presence of the test agent leads to a decrease in the amount or activity of TLR4 in the cell or tissue.

For example, the ability of a test agent to decrease the activity or expression of TLR4 may be tested in a host cell or tissue that expresses TLR4. For example, the amount or activity of TLR4 may be assessed in vitro, in vivo or ex vivo in the liver or in tissue or cells derived from the liver or kidney.

In such a cell-based assay, the TLR4 and/or the test agent may be endogenous to the host cell or tissue, may be introduced into a host cell or tissue, may be introduced into the host cell or tissue by causing or allowing the expression of an expression construct or vector or may be introduced into the host cell or tissue by stimulating or activating expression from an endogenous gene in the cell.

In such a cell-based method, the amount of TLR4 may be assessed in the presence or absence of a test agent in order to determine whether the agent is altering the amount of TLR4 in the cell or tissue, such as through regulation of TLR4 expression in the cell or tissue or through destabilisation of TLR4 protein within the cell or tissue. The presence of a lower TLR4 activity or a decreased amount of TLR4 within the cell or tissue in the presence of the test agent indicates that the test agent may be a suitable antagonist of TLR4 for use in accordance with the present invention in the treatment of an individual having renal dysfunction or renal failure associated with liver disease or brain dysfunction and brain swelling associated with liver disease.

In one embodiment, such a cell based assay may be carried out in vitro or ex vivo on cells or tissue deriving from the patient to be treated. It may therefore be determined whether or not the test agent is capable of decreasing the activity or amount of TLR4 in the cells or tissue of that subject. For example, such a method may be carried out on a sample of cells or tissue from the liver or kidney of the patient.

A method of the invention may use a cell-free assay. For example, the TLR4 may be present in a cell-free environment. A suitable cell-free assay may be carried out in a cell extract. For example, the contacting steps of the methods of the invention may be carried out in extracts obtained from cells that may express, produce or otherwise contain TLR4 and/or a test agent. A cell-free system comprising TLR4 may be incubated with the other components of the methods of the invention such a test agent.

In such a cell-free method, the amount of TLR4 may be assessed in the presence or absence of a test agent in order to determine whether the agent is altering the amount of TLR4 in the cell or tissue, such as through destabilisation of TLR4 protein. In either case, the presence of a lower TLR4 activity or a decreased amount of TLR4 in the presence of the test agent indicates that the test agent may be a suitable antagonist of TLR4 for use in accordance with the present invention in the treatment of an individual having renal dysfunction or renal failure associated with liver disease or brain dysfunction and brain swelling associated with liver disease.

The contacting step(s) of the method of the invention may comprise incubation of the various components. Such incubations may be performed at any suitable temperature, typically between 4° C. and 40° C. Incubation periods may be selected for optimum activity, but may also be optimized to facilitate rapid high-throughput screening. Following the contact and optional incubation steps, the subject methods may further include a washing step to remove unbound components, where such a washing step is generally employed when required to remove label that would give rise to a background signal during detection, such as radioactive or fluorescently labelled non-specifically bound components.

Incubation in cell or cell-free assay systems may be performed in a microtiter plate (e.g. a 96-well plate or other microwell plate). Further, incubation may be performed in an automated fashion (e.g. for high-throughput screening).

A screening method of the invention may be carried out in vivo. For example, a screening method may be carried out in an animal model. In such an in vivo model, the effects of a test agent may be assessed in the liver, or in other organs such as the kidney or heart. Preferably, the animal is a non-human animal such as a rat. For example, a screening method may be carried out in a bile duct-ligated rat model as described in the Examples. As shown in the Examples, bile duct ligation in the rat leads to an increase in TLR4 levels in the kidney of the rat. Such a model may therefore be suitable for identifying agents capable of decreasing TLR4 levels. Accordingly, the screening method of the present invention may comprise the step of administering a test agent to a bile duct ligated rat and determining whether the presence of the test agent leads to a decrease in the amount or activity of TLR4 in the liver, kidney or other organs of the rat.

Such a model may be used to assess the in vivo effects of a test agent. For example, such a model may be used to assess whether the test agent is capable of decreasing the activity or amount of TLR4 in vivo. In such a method, the amount of TLR4 may be assessed and/or the activity of TLR4 may be assessed. Such a model may be used to assess whether the test agent is capable of decreasing the amount of TLR4 that is excreted in the urine.

An in vivo model may also be used to determine whether the test agent has any unwanted side effects. For example, a method of the invention may compare the effects of a test agent on TLR4 with its effects on other receptors in order to determine whether the test agent is specific.

In an in vivo model as described herein, or an in vitro model such as a cell-based or cell-free assay model as described herein, the effects of a test agent on TLR4 may be compared with the effects of the same agent on other Toll like receptors. As discussed above, a preferred TLR4 antagonist for use in a method of treatment as described herein may be an agent that antagonises TLR4, but that does not antagonise other Toll like receptors. The screening methods of the invention may thus include an additional step of assessing whether the test agent has any effect on the activity or amount of one or more other Toll like receptors such as one or more Toll like receptors that are not TLR4. In such a method, a test agent may be identified as a suitable TLR4 antagonist if it is found to decrease the activity or amount of TLR4, but not to decrease, not to significantly decrease, not to significantly decrease, not to alter, or not to significantly alter, the activity or amount of one or more other Toll like receptors in the same assay.

Where the assay is carried out in vivo, for example in a bile duct ligated rat model as described herein, such a method may comprise comparing the amount or activity of TLR4 in the liver, kidney or other organs of the test animal in the presence or absence of the test agent. An observation that the level or activity of TLR4 is decreased in the liver, kidney or other organs of animals treated with the test agent suggests that the test agent may be a suitable antagonist of TLR4. A further finding that treatment with the same test agent does not significantly decrease or alter the levels or activity of one or more other Toll like receptors, may further indicate that the test agent is a suitable specific antagonist of TLR4 that may be used in the methods of treatment described herein.

In the screening methods described herein, the presence of a lower TLR4 activity or a decreased amount of TLR4 in the presence of the test agent indicates that the test agent may be a suitable antagonist of TLR4 for use in accordance with the present invention to treat an individual having liver disease, such as to treat or prevent renal dysfunction or renal failure associated with liver disease or brain dysfunction and brain swelling associated with liver disease.

A test agent that is an antagonist of TLR4 may result in a decrease in TLR4 activity or levels of at least 5%, at least 10%, at least 25%, at least 50%, at least 60%, at least 75%, or at least 85% or more in the presence of the test agent compared to in the absence of the test agent. A test agent that is an antagonist of TLR4 may result in a decrease in TLR4 activity or levels such that the activity or level of TLR4 is no longer detectable in the presence of the test agent. Such a decrease may be seen in the sample being tested or, for example where the method is carried out in an animal model, in particular tissue from the animal such as in the liver or kidney.

A test agent that is an antagonist of TLR4 may be a specific or selective antagonist of TLR as described above. For example, the agent may have an effect on other Toll like receptors, such as antagonism of the activity, signalling or expression of one or more other Toll like receptors, that is less than 25%, less than 20%, less than 15%, less than 10%, less than 5%, less than 1%, or less than 0.1% the effect of that agent on the activity, signalling or expression of TLR4.

Levels or amounts of TLR4 may be measured by assessing expression of the TLR4 gene. Gene expression may be assessed by looking at mRNA production or levels or at protein production or levels. Expression products such as mRNA and proteins may be identified or quantified by methods known in the art. Such methods may utilise hybridisation to specifically identify the mRNA of interest. For example such methods may involve PCR or real-time PCR approaches. Methods to identify or quantify a protein of interest may involve the use of antibodies that bind that protein. For example, such methods may involve western blotting. Regulation of TLR4 gene expression may be compared in the presence and absence of a test agent. Thus test agents can be identified that decrease TLR4 gene expression compared to the level seen in the absence of the test agent. Such test agents may be suitable antagonists of TLR4 in accordance with the invention.

The screening methods may assess the activity of TLR4. For example, such a method may be carried out using peripheral blood mononuclear cells. Such cells will produce cytokines such as TNFα and NFκB on response to stimulation with, for example, lipopolysaccharide (LPS). A screening method may therefore comprise combining peripheral blood mononuclear cells with the test agent or a vehicle and adding LPS. The cells may then be incubated for an amount of time (e.g. 24 hours) to allow the production of inflammatory molecules such as cytokines. The level of cytokines such as TNFα or NFκB produced by the cells in that time period can then be assessed. If the test agent has anti-TLR4 properties, then the production of such cytokines or NFκB should be reduced compared to the vehicle-treated cells.

Further tests may also be carried out in order to confirm that the test agent is suitable for use in the claimed methods. For example, as explained above, a suitable antagonist of TLR4 should be capable of reducing the deleterious consequences of treatment with a hepatotoxin such as acetaminophen (paracetamol). The screening methods of the invention may therefore incorporate further steps, such as those discussed above, which involve assessing the effect of the test agent in an animal treated with such a hepatotoxin and determining whether the effects of that hepatotoxin, such as in injury or dysfunction of organs such as the liver, kidney or brain, are reduced in the presence of the test agent compared to that seen with treatment with the hepatotoxin alone. A suitable TLR4 antagonist will be capable of ameliorating at least some of the effects of the hepatotoxin in the test animal.

Pharmaceutical Formulations

A suitable TLR4 antagonist as described herein is typically formulated for administration with a pharmaceutically acceptable carrier or diluent. The antagonist may be any antagonist as defined herein including any antagonist identified by a screening method of the invention. The antagonist may thus be formulated as a medicament with a standard pharmaceutically acceptable carrier(s) and/or excipient(s) as is routine in the pharmaceutical art. The exact nature of the formulation will depend upon several factors including the desired route of administration. Typically, the antagonist may be formulated for oral, intravenous, intragastric, intravascular or intraperitoneal administration.

The pharmaceutical carrier or diluent may be, for example, an isotonic solution such as physiological saline. Solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with ornithine and at least one of phenylacetate and phenylbutyrate, a pharmaceutically acceptable carrier, e.g. sterile water, olive oil, ethyl oleate, glycols, e.g. propylene glycol, and if desired, a suitable amount of lidocaine hydrochloride.

Where the antagonist to be administered is a nucleic acid molecule, for example where the antagonist is in the form of an expression vector, certain facilitators of nucleic acid uptake and/or expression ("transfection facilitating agents") can also be included in the compositions, for example, facilitators such as bupivacaine, cardiotoxin and sucrose, and transfection facilitating vehicles such as liposomal or lipid preparations that are routinely used to deliver nucleic acid molecules.

A pharmaceutical formulation in accordance with the present invention may further comprise one or more additional therapeutic agents. For example, the formulation may comprise one or more TLR4 antagonists as defined herein. The formulation may comprise one or more TLR4 antagonists as described here and also one or more additional therapeutic agents. Preferably the additional therapeutic agent(s) are agents which will assist in the treatment or prophylaxis of the individual to be treated. For example, one or more agents that are effective at treating liver disease may be administered as part of a formulation as described herein. One or more agents that are effective at treating an underlying liver condition or symptom thereof in the patient may be administered as part of a formulation as described herein.

Treatment

The present invention provides methods for the treatment of individuals having liver disease, particularly for the treatment or prevention of symptoms and conditions associated with or resulting from liver failure or cirrhosis such as renal dysfunction or renal failure or brain dysfunction and/or brain swelling. Accordingly, the invention provides a method of treating an individual having renal dysfunction or renal failure associated with liver disease or brain dysfunction and/or brain swelling associated with liver disease comprising administering to said subject an antagonist of TLR4. Similarly, an antagonist of TLR4 may be provided for use in a method of treating an individual having renal dysfunction or renal failure associated with liver disease or brain dysfunction and brain swelling associated with liver disease. Also provided is the use of an antagonist of TLR4 in the manufacture of a medicament for use in the treatment of an individual having renal dysfunction or renal failure associated with liver disease or brain dysfunction and brain swelling associated with liver disease.

The antagonist may be any antagonist as described herein including any antagonist identified by a screening method of the invention. The antagonist may be provided in a formulation as described herein. An antagonist of TLR4 as described herein is thus administered to a subject in order to treat or prevent renal dysfunction or renal failure associated with liver disease or brain dysfunction and brain swelling, or particular symptoms or conditions associated with renal dysfunction or renal failure or brain dysfunction and brain swelling in the subject. An antagonist of TLR4 as described herein can thus be administered to improve the condition of a subject, for example a subject suffering from liver disease, cirrhosis, renal dysfunction or renal failure associated with liver disease or paracetamol overdose or brain dysfunction and brain swelling associated with liver disease or paracetamol overdose. An antagonist of TLR4 as described herein may be administered to alleviate the symptoms of a subject, for example the symptoms associated with liver disease, cirrhosis, renal dysfunction or renal failure associated with liver disease or paracetamol overdose or brain dysfunction and brain swelling associated with liver disease or paracetamol overdose. An antagonist of TLR4 as described herein may be administered to combat or delay the onset of portal hypertension or any symptom associated therewith, such as varices. The invention can therefore prevent the medical consequences of cirrhosis. Use of an antagonist of TLR4 as described herein may thus extend the life of a patient with liver disease or liver failure.

The treatment of liver disease, or the treatment of an individual having liver disease, as described herein, refers to the treatment of an individual having liver disease. The individual may be suffering from liver failure, such as acute liver failure (ALF) or acute on chronic liver failure (ACLF). The individual may be suffering from chronic liver disease such as cirrhosis or alcoholic cirrhosis. The patient may be suffering from liver disease or cirrhosis associated with or caused by an infection such as a hepatitis virus infection such as hepatitis C virus infection. The patient may be suffering from liver disease or cirrhosis associated with or caused by treatment with a hepatotoxin such as acetaminophen (paracetamol). The methods described herein may be used in the treatment of any such disease.

The individual may be suffering from one or more symptoms or conditions caused by or associated with liver disease or cirrhosis. Any one or more of these conditions or symptoms may be treated in accordance with the present invention. For example, the individual may be suffering from, or at risk of, one or more of the following as a result of their liver disease or cirrhosis: renal dysfunction; renal failure; HRS; increased plasma creatinine; brain dysfunction and brain swelling increased plasma ammonia; increased liver enzyme concentrations (such as increased concentrations of ALT and/or AST in the liver); increased inflammation, injury and/or dysfunction in the liver and/or kidney and/or brain and/or blood circulation; liver tissue damage resulting from liver failure, such as resulting from acetaminophen (APAP) toxicity. The individual may be suffering from, or at risk of, acute liver failure, alcoholic hepatitis and/or reperfusion injury of the liver. Those conditions may result from the liver disease or cirrhosis of the individual. The methods and uses described herein may be of utility in the treatment or prevention of any one or more of these symptoms or conditions, particularly, in an individual suffering from liver disease.

In particular, the methods described herein may be used in the treatment of a patient having renal dysfunction as a result of liver disease. For example, the patient may have or be at risk or renal failure. The patient may have cirrhosis. The patient may not have HRS. For example, the patient may not have reduced renal blood flow. The liver disease and/or renal dysfunction may result from an infection and/or inflammation. The liver disease and/or renal dynsfunction may result from exposure to a hepatotoxin such as acetaminophen (paracetamol) such as exposure to a high level of the hepatotoxin, such as an overdose with paracetamol. The methods described herein may be used to treat or prevent any of these conditions or symptoms, particularly to treat or prevent the renal dysfunction resulting from such a condition or exposure.

As described herein, the antagonist of TLR4 may lead to decreased expression and/or decreased levels of TLR4 in the liver and/or kidney of the subject. For example, the antagonist may be an agent that inhibits transcription of TLR4 in cells of the subject.

As described herein, the antagonist of TLR4 may lead to decreased activity of TLR4 in the liver and/or kidney of the individual.

The subject is treated with an antagonist of TLR4 as described herein. As described above, the antagonist of TLR4 may be administered alone or in the form of a pharmaceutical formulation. The formulation may comprise one or more antagonists of TLR4 and may comprise one or more additional therapeutic or prophylactic agents.

Two or more different TLR4 antagonists as described herein may be used in combination to treat a subject. The two or more antagonists may be administered together, in a single formulation, at the same time, in two or more separate formulations, or separately or sequentially as part of a combined administration regimen.

An antagonist or formulation of the invention may be administered by any suitable route. Preferably it is administered by oral, intravenous, intragastric, intraperitoneal or intravascular routes. The antagonist or formulation may be administered directly to the liver of the subject.

The antagonist is administered in a therapeutically effective amount. A suitable dose of an antagonist of the invention can be determined according to various parameters such as the age, weight and condition of the subject to be treated; the type and severity of the liver disease; the route of administration; and the required regimen. A suitable dose can be determined for an individual antagonist. For example, for some antagonists a typical dose may be in the order of from 0.1 mg/kg/day to 30 g/kg/day. A physician will be able to determine the required dosage of antagonist and for any particular subject.

The present invention is broadly applicable to therapeutic methods and is relevant to the development of prophylactic and/or therapeutic treatments. It is to be appreciated that all references herein to treatment include curative, palliative and prophylactic treatment.

Prophylaxis or therapy includes but is not limited to eliciting an effective decrease in TLR4 amount, function or activity in order to cause a reduction in one or more symptoms or conditions associated with, or resulting from, liver disease, liver failure or cirrhosis such as renal dysfunction or renal failure or brain dysfunction and/or brain swelling. The symptoms or conditions may be, for example, any of those discussed above. For example, prophylaxis or therapy may result in: reduced symptoms of renal dysfunction, prevention or reduced symptoms of liver failure, reduced levels of plasma creatinine, plasma ammonia, liver enzyme concentrations (such as reduced concentrations of ALT and/or AST in the liver), reduced inflammation in the liver and/or kidney and/or brain and/or blood circulation, and or a reduction in liver tissue damage resulting from liver failure, such as resulting from acetaminophen (APAP) toxicity. Prophylaxis or therapy may result in the maintenance of a particular level of renal dysfunction, renal failure, plasma creatinine, brain dysfunction and/or brain swelling, plasma ammonia, liver enzyme concentrations (such as concentrations of ALT and/or AST in the liver), inflammation in the liver and/or kidney and/or brain and/or blood circulation, and or liver tissue damage resulting from liver failure, such as resulting from acetaminophen (APAP) toxicity, in a patient where such symptoms have been increasing or are expected to increase as a result of the liver disease, liver failure and/or cirrhosis. Prophylaxis or therapy may result in such changes in symptoms or conditions in such an individual changing at a reduced rate compared to the changes that would have been seen or would have been expected in the absence of such treatment.

Prophylaxis or therapy may have similar effects in relation to any of the symptoms or consequences of liver disease, liver failure or cirrhosis described herein. That is, treatment in accordance with the present invention may lead to a lessening in the severity of such symptoms or consequences, maintenance of an existing level of such symptoms or consequences or a slowing or reduction in the worsening of such symptoms or consequences.

Patients to be Treated

The present invention relates to the treatment or prevention of renal dysfunction or renal failure or brain dysfunction and/or brain swelling in individuals in need thereof. An individual to be treated in accordance with the present invention may therefore have liver disease such as cirrhosis or may be at increased risk of liver disease such as cirrhosis. For example, the subject may have liver failure. The subject may have renal failure or brain dysfunction and/or brain swelling.

Methods for diagnosing liver failure, renal dysfunction, brain dysfunction, brain swelling or HRS are well known in the art and in particular to clinicians and veterinarians in the field. For example, renal dysfunction and HRS are characterised by a reduction or loss of renal function, which may be assessed by monitoring urine volume, or sodium concentration and osmolality of the urine. HRS is also associated with a reduction in renal blood flow. Preferably, the subject will have been diagnosed as having liver failure and/or HRS, for example by a medical or veterinarian professional. The subject may display one or more symptoms associated with liver failure, renal dysfunction or renal failure.

The individual to be treated may have increased expression of TLR4 in the liver and/or kidney compared with a healthy individual, such as an individual not having liver disease or renal dysfunction. The individual to be treated may have increased expression of TLR4 in the renal tubules compared with a healthy individual, such as an individual not having liver disease or renal dysfunction. The individual to be treated may have increased urinary TLR4 compared with a healthy individual, such as an individual not having liver disease or renal dysfunction.

A patient may be identified as being suitable for treatment as described herein by a method comprising measuring the level of TLR4 in the urine of the patient and comparing the level of urinary TLR4 with the level of urinary TLR4 from a healthy individual, such as an individual not having liver disease or renal dysfunction. In such a method, an increased level of urinary TLR4 indicates that the patient may be suitable for treatment according to the present invention.

The individual to be treated may have been diagnosed as suffering from acute liver failure, cirrhosis, renal dysfunction and/or renal failure, or one or more symptoms or conditions as described herein that may be associated with such conditions, for example by any of these methods. The individual to be treated may have been diagnosed as being at risk of liver failure, cirrhosis, renal dysfunction and/or renal failure or such symptoms or conditions. For example, the individual may have been diagnosed with one or more symptoms that are associated with liver failure, cirrhosis, renal failure and/or renal failure. For example, the individual to be treated may have liver cirrhosis, alcoholic hepatitis, idiopathic non-cirrhotic portal hypertension, congenital hepatic fibrosis, partial nodular transformation, Budd-Chiari syndrome, portal vein thrombosis, right heart failure or schistosomiasis infection.

The subject to be treated may be any individual which is susceptible to liver disease such as liver failure. The subject may be male or female. Women may be more susceptible to the adverse effects of alcohol than men. Women can develop alcoholic chronic liver disease in a shorter time frame and from smaller amounts of alcohol than men.

The subject to be treated may be a human. The subject to be treated may be a non-human animal. The subject to be treated may be a farm animal for example, a cow or bull, sheep, pig, ox, goat or horse or may be a domestic animal such as a dog or cat. The subject may or may not be an animal model for liver disease. The animal may be any age, but will often be a mature adult subject.

Biomarkers for Diagnosis

As explained above, the present invention relates to renal dysfunction, brain dysfunction and brain swelling in patients suffering from liver disease, such as cirrhosis.

The most commonly used indicator of renal function is to measure the level of creatinine in the blood. However, a rise in blood creatinine level is observed only with marked damage to functioning nephrons. Therefore, this test is not suitable for detecting early-stage kidney disease. There is therefore a need for an alternative test that can be used to identify kidney disease at an early stage.

As reported in the examples, the Inventors have unexpectedly found that there are detectable changes in the kidneys in individuals having renal dysfunction associated with liver disease such as cirrhosis. This means that it may be possible to detect kidney disease, such as renal dysfunction, or kidney failure at a much earlier stage than possible by monitoring plasma creatinine levels. The inventors have found that the onset of renal dysfunction is associated with expression of TLR4 in the kidney, particularly tubular expression of TLR4 and is also associated with damage to the proximal tubules in the kidney. The inventors have also found that urinary TLR4 levels increase in such patients. Furthermore, urinary TLR4 levels are even higher in patients who go on to suffer from renal failure. Any of these factors may be used to detect or predict kidney disease such as renal dysfunction, or kidney failure, in an individual as described herein who is suffering from, or at risk of, liver disease or liver failure. For example, these factors may be used to detect kidney failure or an increased risk of kidney failure in an individual at risk thereof, such as an individual having liver disease, an individual having, or at risk of, liver failure or an individual having liver cirrhosis.

Accordingly, a method is provided for the detection or prediction of kidney injury, kidney failure in an individual as described above who is suffering from liver disease. The individual may be any of the individuals as described above under the heading "patients to be treated".

As reported in the Examples, the inventors have found that TLR4 expression is increased in the kidney, particularly in the tubules in patients having renal dysfunction. For example, a method of diagnosing renal dysfunction or renal failure or of predicting renal failure in a patient having liver disease or cirrhosis may comprise the steps of (a) detecting the expression or expression pattern of TLR4 in the kidney of the patient and (b) comparing the expression level or expression pattern of (a) with a control level or pattern of TLR4 expression based on the expression of TLR4 found in the kidney of a healthy individual such as an individual not suffering from either liver disease or renal dysfunction. The method may comprise measuring the level or expression of TLR4 in a kidney of the patient and in the kidney of a control individual such as a healthy individual described above and comparing the level or expression of TLR4 in the two samples. The method may comprise measuring the level or expression of TLR4 in the kidney of the patient and comparing that level with a known control level or expression pattern based on earlier measurements from a control individual or group of control individuals as described above.

In such methods, the measurements may be made on a sample from the kidney, such as a kidney biopsy sample. The sample of the kidney may comprise a sample from the glomeruli or the renal tubules. Such a sample may comprise the apical brush border of the renal tubules.

In such methods, an increased level of TLR4 expression in the kidney of the patient compared with the control level indicates that the patient has an increased likelihood of, an increased risk of or that the individual is already suffering from, renal dysfunction or renal failure. An increased level of TLR4 expression in the kidney tubules of the patient compared with the control level indicates that the patient has an increased likelihood of, an increased risk of or that the individual is already suffering from, renal dysfunction or renal failure.

Methods are also provided which utilise the findings of the present inventors that urinary TLR4 levels are increased in renal dysfunction.

For example, a method of diagnosing renal dysfunction or renal failure or of predicting renal failure in a patient having liver disease or cirrhosis may comprise the steps of (a) measuring the level of TLR4 in the urine of the patient and (b) comparing the level of (a) with a control level of TLR4 based on the level of TLR4 found in the urine of a healthy individual such as an individual not suffering from either liver disease or renal dysfunction. The method may comprise measuring the level of TLR4 in a urine sample from the patient and in a urine sample from a control individual such as a healthy individual described above and comparing the levels of TLR4 in the two samples. The method may comprise measuring the level of TLR4 in a urine sample from the patient and comparing that level with a known control level based on earlier measurements from a control individual or group of control individuals as described above. In such methods, an increased level of urinary TLR4 in the patient compared with the control level indicates that the patient has an increased likelihood of, an increased risk of or that the individual is already suffering from, renal dysfunction or renal failure.

A further method may be used to predict whether the patient is likely to suffer from renal failure. This information may be used by a clinician to determine how the patient is treated and their condition monitored. Such a method may comprise the steps of (a) measuring the level of TLR4 in the urine of the patient and (b) comparing the level of (a) with a known level of TLR4 based on the level of TLR4 found in the urine of a control individual suffering from liver disease and renal dysfunction who did not go on to suffer renal failure. The method may comprise measuring the level of TLR4 in a urine sample from the patient and in a urine sample from the control individual and comparing the levels of TLR4 in the two samples. The method may comprise measuring the level of TLR4 in a urine sample from the patient and comparing that level with a known control level based on earlier measurements from a control individual as described above. In such methods, an increased level of urinary TLR4 in the patient compared with the control level indicates that the patient has an increased likelihood of, an increased risk of or the individual is already suffering from, renal failure.

An increased level of urinary TLR4 or of TLR4 expression in these methods when compared with a control level may be a statistically significant increase in urinary TLR4 concentration or TLR4 expression level. An increased level of urinary TLR4 or TLR4 expression in these methods may be an increase of at least 15%, at least 25%, at least 50%, at least 75%, at least 100%, at least 200%, at least 300% or more when compared to a suitable control. The control may be the urinary TLR4 level from a single control individual or may be an average value obtained from a group of control individuals.

The method may comprise testing a sample from the individual for the presence of one or more markers of renal failure or renal decompensation. The presence of such markers in the sample from the individual may indicate that the individual is suffering from renal failure, or that the individual is in the early stages of, or is at increased risk of, renal failure. The markers may be markers associated with damage to the glomeruli or the renal tubules. For example, if the sample is a sample of urine, the sample may be tested for the presence of (a) a combination of IL-18 (interleukin-18) and KIM-1 (kidney injury molecule 1), and/or (b) urinary LFABP (liver fatty acid binding protein). If the sample is a sample of serum, the sample may be tested for the presence of one or more markers selected from (a) IL-6 (interleukin-6) and/or IL-10 (interleukin-10) and/or TNFα, (b) MMP-9 (matrix metalloproteinase 9), (c) NAG (N-Acetylglucosamine), (d) myeloperoxidase and (e) glutathione S transferase. If samples of serum and urine are both available, both such samples may be tested for one or more of cystatin C, NGAL (neutrophil gelatinase associated lipocalin), osteopontin and beta-2-microglobulin and/or for a combination of KIM-1 and IL-18. Any combination of these markers may be used, optionally with additional markers not specifically mentioned here. Preferably more than one of the markers mentioned above is assessed, such as at least two, at least three, at least four or at least five of these markers.

As explained above, the method may comprise testing a sample of kidney from the individual for the expression of TLR4. The expression of TLR4 in the kidney of the individual indicates that the individual may have renal failure, or that the individual may be in the early stages of, or at increased risk of, renal failure.

The methods described herein may further comprise testing a sample of kidney from the individual for the expression of one or more inflammatory modulators, such as NFkB, IL-6 or TNFα. Expression of one or more such inflammatory modulators indicates that the individual may have renal failure, or that the individual may be in the early stages of, or at increased risk of, renal failure.

In the methods described herein, the sample of the kidney may comprise a sample from the glomeruli or the renal tubules. Expression of TLR4 in such a sample may indicate that the individual has kidney failure, or that the individual may be in the early stages of, or at increased risk of, renal failure. Such a sample may comprise the apical brush border of the renal tubules. Expression of TLR4 in such a sample may indicate that the individual has kidney failure, or that the individual may be in the early stages of, or at increased risk of, renal failure.

A method may comprise assessing the kidney of the patient, such as the glomeruli or renal tubules or apical brush border of the proximal renal tubules, for renal disease. Any suitable method may be used. The method may be carried out on a sample from the individual, such as a sample of kidney as described above. The method may be carried our by directly assessing the structure or function of the kidney, or the proximal renal tubules, in vivo. The presence of abnormal structure or function, such as a diseased or damaged structure or reduced function, may indicate that the individual has kidney failure or HRS, or that the individual may be in the early stages of, or at increased risk of, renal failure or HRS.

An individual who has been identified by any such method as having, or being at risk of, renal dysfunction or renal failure, may then be provided with appropriate therapeutic or preventative treatment for that condition. This may allow suitable treatment to be provided earlier than would have been possible when detecting renal dysfunction or renal failure using creatinine levels. An individual who has been identified by any of these methods as having, or being at risk of, renal dysfunction or renal failure, may then be treated by any of the therapeutic or prophylactic methods described herein.

A method may also be provided in order to identify further suitable biomarkers that could be used in the detection methods described herein. This may involve comparing samples obtained from individuals having renal failure or renal dysfunction linked to liver disease with samples obtained from a normal individual or an individual not having renal failure or renal dysfunction or liver disease. The method may involve identifying markers that can distinguish between a sample from a renal failure/renal dysfunction individual and a sample from a normal individual.

A suitable marker may be identified using samples from the organism of interest, such as samples from human individuals. A suitable marker may be identified using samples from an animal model, such as the bile duct ligated (BDL) rat or the BDL rat treated with endotoxin or lipopolysaccharide. Such samples may be compared with samples from a normal or sham treated rat.

The sample may be any suitable sample that can be readily retrieved from a suitable individual, such as a sample of urine, plasma, serum or blood. The marker may be a protein or other molecule that is present in one of the samples, but not in the other sample, or that is present in significantly different amounts in the two samples, such that the samples can be distinguished on the basis of that molecule. A marker that is identified in this way as being capable of distinguishing between the two types of sample may be used in a method as described above in order to determine whether or not an individual, particularly an individual having liver disease, has, or is at risk of, renal failure or renal dysfunction. This may be achieved by comparing the presence, absence or amount of the marker in a sample obtained from the individual of interest with the known presence, absence or amount of that marker in known samples, and thereby correlating the sample from the individual with either a control sample from a normal individual or a diseased sample from an individual having renal dysfunction or renal failure associated with liver disease.

EXAMPLES

Example 1: Role of TLR4 in Acute Liver Failure 3 groups of Cd1 male mice were studied. Sham, APAP (acetaminophen, 500 mg/kg single dose IP after overnight fasting), APAP+TLR4 antagonist (STM28; 20 ug, 1 hour prior to the administration of APAP and 6 hours later). Blood was collected for biochemistry and cytokine assay. Liver, Kidney and Brain were collected for western blot and cytokine analyses and the brain frontal cortex for brain water. Animals were sacrificed at 12 hours after APAP administration.

Figure 4:
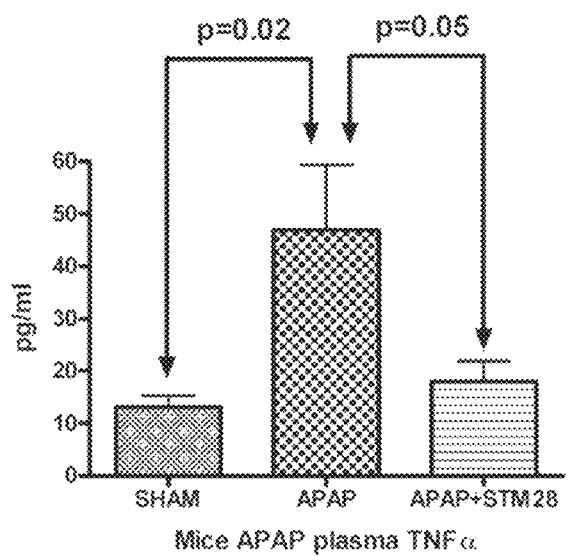
Figure 5:
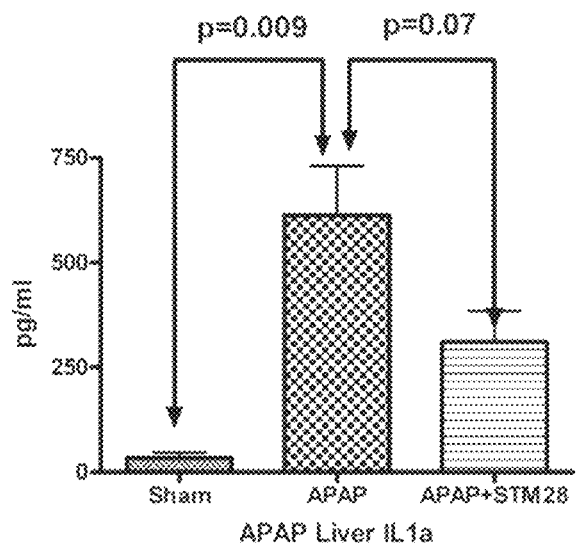
Figure 6:
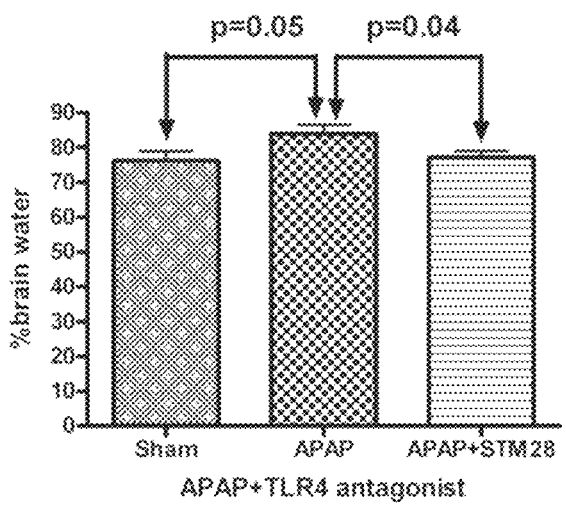
Figure 7:
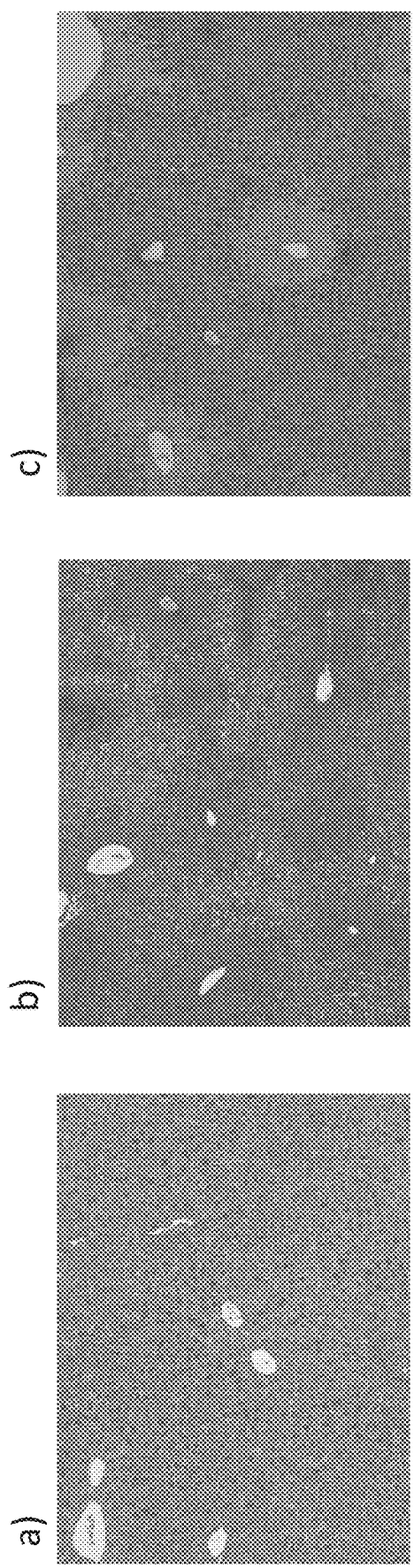

Acetaminophen (APAP) toxicity is manifested by rapid acute liver injury, severe brain edema and renal failure. Unregulated inflammation in such an instance leads to the release of cytokines along with activation of NFkB and progressive liver injury. Administration of APAP (500 mg/kg) to the mice led to an increase in liver enzymes ALT ($p=0.004$) and AST ($p=0.007$) (FIG. 1A). Administration of a novel TLR4 antagonist (STM28) significantly reduced the [ALT($p=0.01$) and AST ($p=0.008$) (FIG. 1A). Multiorgan failure was manifested by an increase in Ammonia and creatinine ($p=0.001$ and $p=0.004$) respectively. STM28 significantly reduced Ammonia ($p=0.03$) and creatinine ($p=0.09$) (FIG. 1B). APAP induces apoptosis and necrosis leading to progressive liver injury. NFkB has been implicated in mediating hepatoprotective effect via prosurvival pathway and inhibiting apoptosis. STM28 (TLR4 antagonist) in the APAP group restored the NFkBp65 in Liver, thereby promoting hepatocyte survival (FIG. 2A). As opposed to the NFkB in Liver, there was an increase expression of NFkBp65 in Brain and Kidney in the APAP group ($p=0.02$) each. APAP group treated with STM28 showed a reduction in the NFkBp65 protein expression in Kidney and Brain ($p=0.02$) and ($p=0.04$) respectively (FIG. 2B). APAP led to a massive surge in the TNFα levels in the Liver and in Kidney which contributes to the pathophysiological inflammatory changes. Administration of TLR4 antagonist (STM28) ameliorated this response to an extent in both Liver and Kidney (FIG. 3). An increase in tissue TNFα was associated with a concomitant rise in the plasma TNFα levels in APAP toxicity. STM28 abrogated this rise of TNFα in the treatment group (FIG. 4). IL1A plays an important role in promoting apoptosis and necrosis. We found a significant rise in the IL1A levels in the APAP liver, this was reduced remarkably in APAP group treated with STM28 (FIG. 5). Coma in ALF patients is contributed by inflammation and progressive brain swelling. There was an increase in brain edema as ascertained by the measuring brain water in APAP group, this was successfully reverted in the APAP group treated with STM28 (FIG. 6). Acetaminophen (APAP) toxicity led to profound centrilobular necrosis as shown in FIG. 7 slide b). Treatment with STM28 (TLR4 antagonist) and markedly reduced the extent of injury as shown in FIG. 7 slide c), FIG. 7 slide a) shows normal liver for comparison. The results of this study show for the first time a role for TLR4 in pathogenesis of multiorgan failure in ALF. The data strongly support a potential therapeutic role for TLR4 antagonist in the prevention of Acute Liver Failure.

Example 2: Role of TLR4 in Renal Dysfunction in Liver Disease

These experiments utilised an established animal model of cirrhosis, the bile duct ligated (BDL) rat. BDL rats may be generated by methods known in the art. For example, male Sprague-Dawley rats (200-250 g) may be used for this procedure. Following anaesthetisation, a mid-line laparotomy may be performed, the bile duct exposed, triply ligated with 4.0 silk suture, and severed between the second and third ligature. The wound is then closed in layers with absorbable suture, and the animal allowed to recover in a quiet room before being returned to the animal storage facility.

6 groups of Sprague-Dawley rats were studied: n=6 in each group. Sham operated (these were used as a control group who had an abdominal laparotomy). Sham operated+ LPS, (control group with and additional dose of Lipopolysaccharide (LPS). Bile Duct Ligation (BDL):4 weeks, a chronic model of BDL at 4 weeks has been used to study Hepatorenal syndrome. BDL+Norfloxacin: Norfloxacin is commonly used antibiotic in the treatment of infection of the ascitic fluid (Spontaneous bacterial peritonitis) in patients with cirrhosis. BDL+LPS (1 mg/kg); BDL with an additional (LPS) mimics the organ dysfunction which is commonly found in patients with acute decompensation of cirrhosis. BDL+Norfloxacin+LPS. Where used, Norfloxacin 20 mg/kg was gavaged orally for 10 days.

The aims of this study was to determine (1) Whether cirrhosis is associated with an upregulation of TLR4, NFkB and proinflammatory cytokines in kidney. (2) Whether selective decontamination of the gut with Norfloxacin would result in a reduction in TLR4 expression, attenuate NFkB and cytokines and make Kidney less susceptible to further endotoxemic insult.

Biochemistry: Functional aspect of Kidneys was assessed by measuring plasma creatinine. Protein expression of TLR4 and NFkBp65 was assessed using a commonly used Western Blot technique. Localisation of TLR4 and Caspase (effector protein leading to cell death) was done by Immunohistochemistry. Cytokines were quantified using the ELISA bead array.

Figure 8:
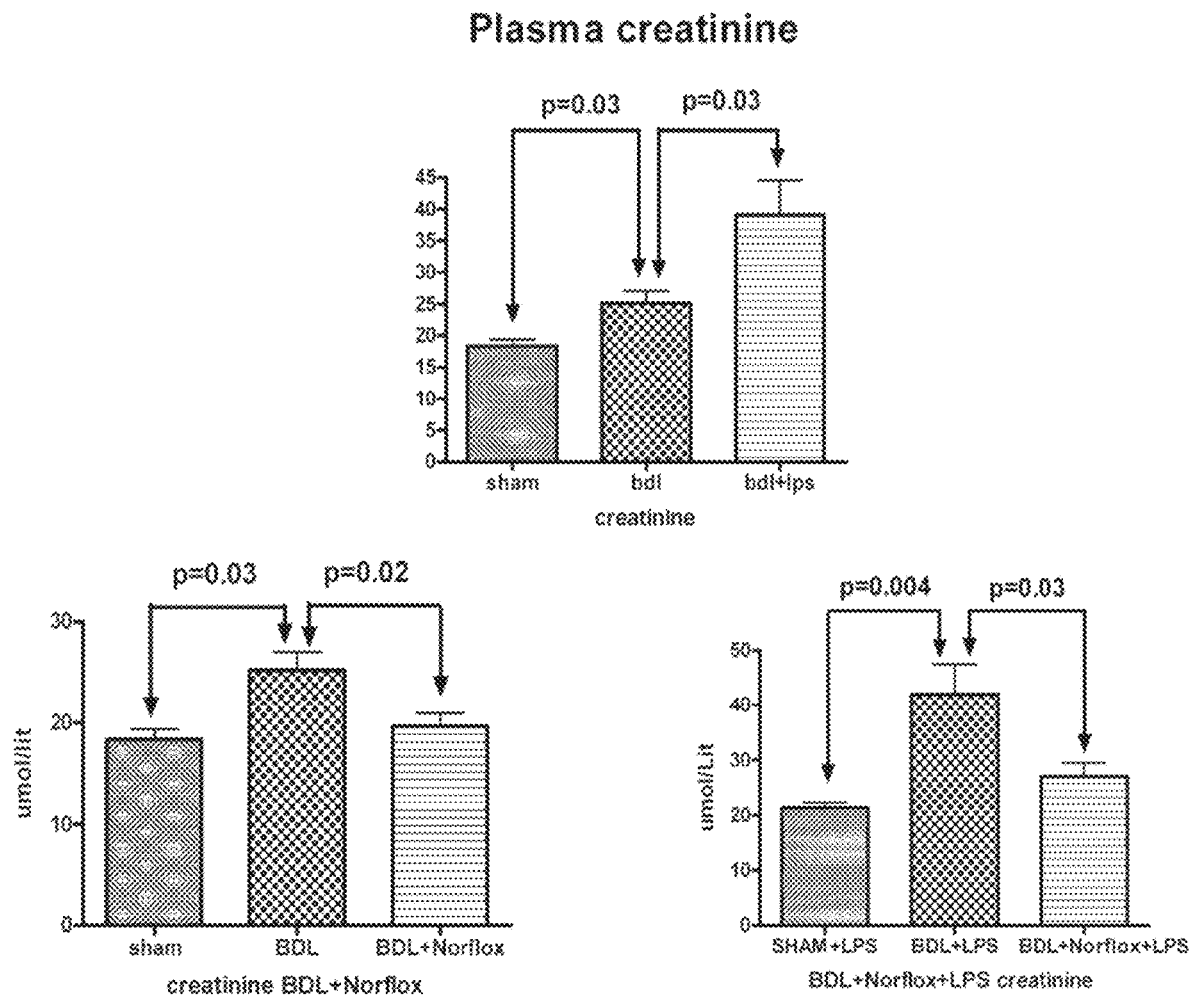
Figure 11:
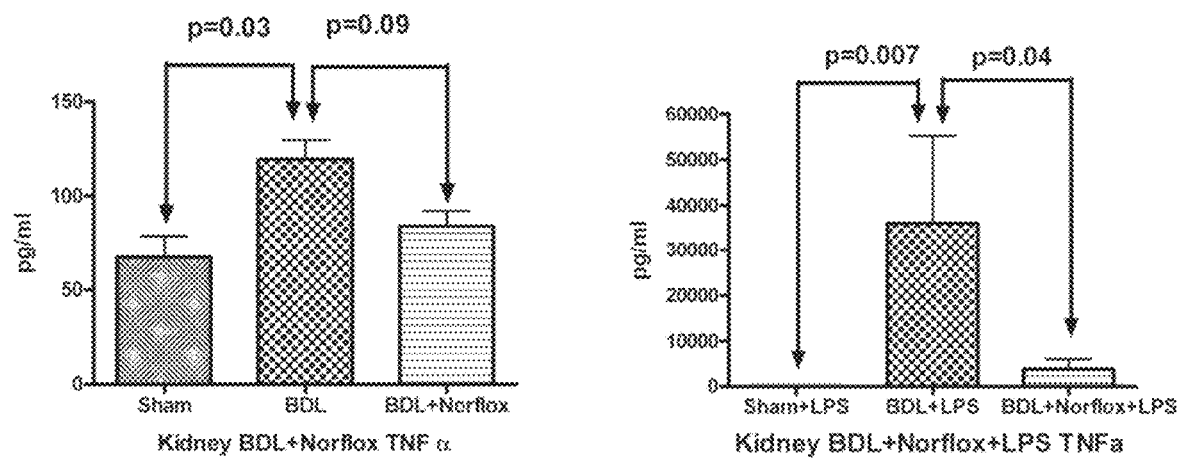
Figure 12:
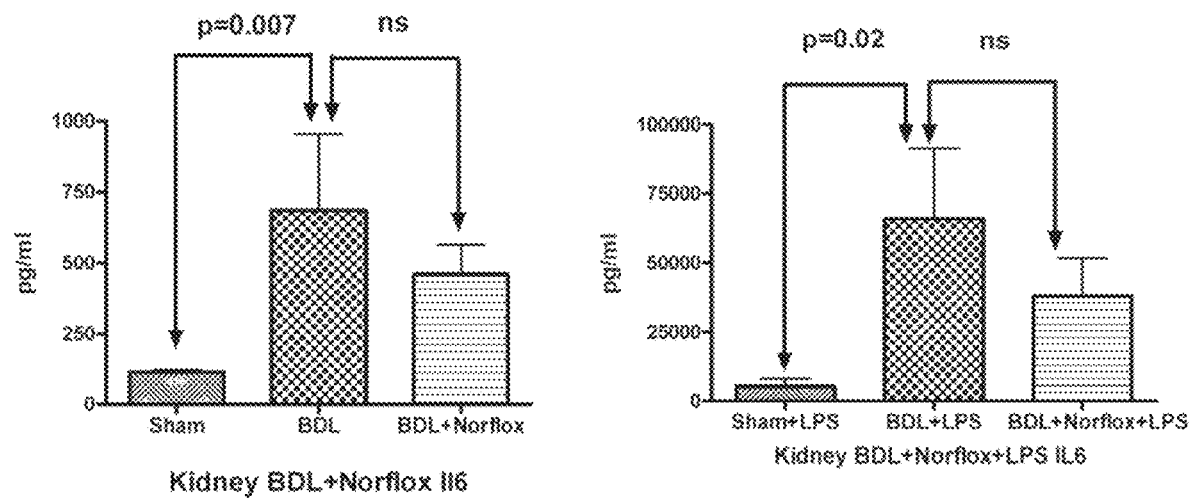
Figure 13:
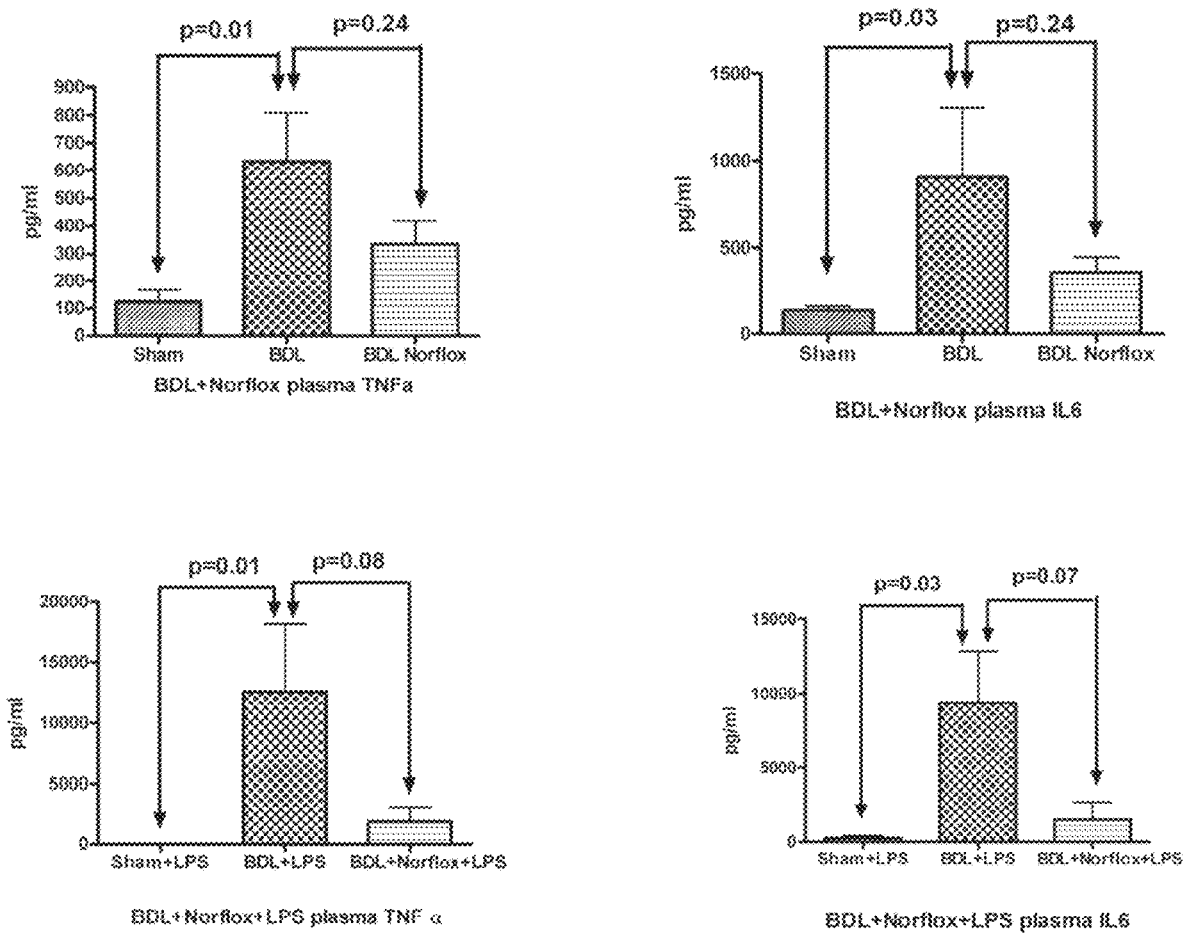

Creatinine represents the renal function which is raised in the BDL rat and BDL+LPS rat plasma as compared to sham and sham+LPS ($p=0.03$ and $p=0.004$) respectively. Administration of Norfloxacin these groups led to a reduction in the creatinine in BDL and BDL+LPS rats ($p=0.02$ and $p=0.03$) respectively (FIG. 8). Cirrhosis associated endotoxemia primes the kidney leading to an upregulation of TLR4 (LPS ligand) making the kidney susceptible to further endotoxemia as evident by an upregulation of TLR4 protein expression using Western Blot in BDL and in BDL+LPS rat kidney compared to sham and sham+LPS ($p=0.03$ and $p=0.05$) respectively. Selective decontamination with Norfloxacin 20 mg/kg orally for 10 days reduced the TLR4 expression in both BDL and in the BDL group administered LPS ($p=0.02$ and $p=0.02$) respectively (FIG. 9). NFkBp65, an important adaptor in promoting the inflammatory cascade is activated in the kidney following TLR4 stimulation in both BDL and in the BDL rats administered with LPS as compared to their control sham groups ($p=0.02$ and $p=0.03$) respectively. Selective decontamination with Norfloxacin in both the groups attenuated the expression of the NFkBp65 expression in Kidney ($p=0.02$ and $p=0.01$) respectively (FIG. 10). Activation of TLR4 in the BDL model of cirrhosis also led to a local inflammatory response in the kidney leading to local damage as evident by an increase in the TNFα both in the BDL and BDL group further administered with LPS. Selective decontamination prevented the rise in the TNFα, thereby limiting the damage (FIG. 11). It was also associated with a significant increase in the Kidney IL6 in both BDL and BDL group administered LPS. Treatment with Norfloxacin had no effect on the local IL6 production (FIG. 12). Activation of the TLR4 led to a surge in the proinflammatory cytokines (TNFα and IL6) systemically in BDL and BDL+ LPS group which can perpetuate the inflammatory response. Treatment with Norfloxacin ameliorated the inflammatory response by reducing the secretion of cytokines (FIG. 13). Haematoxylin and eosin staining of the Kidney showed no apparent change in the different groups as seen in FIG. 14. Administration of LPS (endotoxin) in the control sham group led to the upregulation of TLR4 at the apical brush border of the proximal renal tubules. This was more pronounced in the BDL group administered LPS with the expression in the apical brush border and extending into the proximal tubular cells, this was associated with vacuolar degeneration of the proximal renal tubules (see FIG. 15). Activation of the TLR4 pathway leads to secretion of TNFα which triggers the death receptor pathway stimulating the effector protein caspase 3 promoting cell death and reduced kidney function as evident in the BDL and the BDL group administered LPS. Selective decontamination with Norfloxacin led to a reduction in the cell death as shown by a reduction in the caspase positivity, thereby improving renal function (see FIG. 16). Our data provide strong evidence indicating an important role of TLR4 in mediating susceptibility to the development of renal dysfunction in an experimental of cirrhosis following inflammation/infection. Selective gut decontamination with Norfloxacin attenuated this pathological inflammatory process and prevents renal failure induced by LPS.

Example 3: Increased Renal Tubular Expression of TLR4 in Cirrhosis

Kidney biopsies were studied from 7 cirrhotic patients who presented with renal failure. Various measures were recorded for these patients as set out in Table 1 below. Transjugular Renal biopsies were performed on patients who presented with proteinuria>0.5 gm/day and/or microscopic haematuria and/or unexplained high levels of serum creatinine. Clinical data on the demographics, etiology and the biochemical parameters were collected retrospectively. Paraffin embedded Kidney sections were stained immunohistochemically with antimouse primary TLR4 (1:100, Life span bioscience, cat no LS-B2070) antibody following deparaffinisation and dehydration using the citrate Antigen retrieval method. Liver biopsy cores from patients with decompensated alcohol liver disease and patients with alcoholic hepatitis were stained for antimouse TLR4 antibody using the protocol above. The results are presented in Table 1 below and in FIGS. 17 and 18. Increased tubular TLR4 staining correlated with a diagnosis of acute kidney injury rather than hepatorenal syndrome.

Example 4: Urinary TLR4 Concentration Increased in Those Cirrhotic Patients Who go on to Develop Renal Failure We found that the increased expression of renal tubular TLR4 identified in Example 3 can also be identified by measuring urinary TLR4 concentration. We also found that levels of urinary TLR4 are higher in those cirrhotic patients that go on to develop renal failure. Urine samples from the healthy controls, patients with decompensated cirrhosis and patients with decompensated cirrhosis who presented to the hospital with acute inflammatory insult were collected. Urine from all the cohorts was concentrated using the centrifugal filter units (Millipore) for 5000 rpm for 5 minutes at 4° C. Equal amount of the urine was loaded using the loading buffer. The protein was separated using the gel electrophoresis. The membrane was probed with a commercially available anti-rabbit TLR4 overnight for 16 hours @ 4° C. (1:1000, abbiotec) and also using the anti mouse antibodies (C3-31 and 125-2, Innaxon) which are currently under development for the fast western blot analysis. Protein quantification in both the membranes were ascertained using a public domain, Java-based image processing program; Image J. TLR4 protein quantification was corrected for urine creatinine. FIG. 19A shows a Western Blot of urine samples showing the detection of TLR4 in the urine. TLR4 was detected in those patients diagnosed as having acute kidney injury (see Example 3) but not in healthy patients or patients diagnosed with hepatorenal syndrome.

TABLE 1

Kidney biopsies from cirrhotic patients presenting with renal failure

| | patient 1 | patient 2 | patient 3 | patient 4 | patient 5 | patient 6 | patient 7 |
|---|---|---|---|---|---|---|---|
| Aetiology | ALD | ALD | ALD + HCV | ALD | ALD | ALD | ALD |
| ascites | Yes | Yes | Yes | Yes | Yes | Yes | Yes |
| bilirubin (μmol/L) | 424 | 93 | 12 | 29 | 52 | 14 | 20 |
| creatinine (μmol/L) | 135 | 128 | 104 | 125 | 187 | 112 | 104 |
| antibiotics | yes | no | no | yes | no | no | no |
| Outcome | Dead | LT | Alive | LT | LT | LT | LT |
| Diagnosis | AKI | HRS | HRS | AKI | HRS | HRS | HRS |
| Tubular TLR4 staining | +++ | + | − | +++ | − | + | + |
| Evidence of cell death | +++ | + | − | +++ | − | − | + |

ALD: Alcoholic liver disease; HCV: Hepatitis C Virus; HRS: Hepatorenal Syndrome; AKI: Acute kidney injury; LT: Liver Transplantation.

FIG. 19B shows the measurement of urinary TLR4 in a population of healthy volunteers and cirrhotic patients. The values of urinary TLR4 were very low in the healthy volunteers and patients with compensated or decompensated cirrhosis and not different to each other. Patients with HRS had a low urinary TLR4 as well. However, patients with cirrhosis and superimposed inflammation and infection who were at risk of developing renal failure had higher TLR4 levels in their urine. In the patients that developed renal failure the values of urinary TLR4 were significantly higher. These data suggest that urinary TLR4 values may predict the development of renal failure and define a population of patients that should be treated with a TLR4 antagonist.

Example 5: Administration of TLR4 Antagonists in BDL Mice

These experiments used an animal model of cirrhosis due to bile duct ligation. We showed that administration of STM 28, an antagonist of TLR4 inhibits inflammation and improves renal dysfunction without improving liver function. This study was performed in Bile Duct Ligated (BDL) cirrhotic mice. The animals were treated with STM28, which is an inhibitor of TLR4, or placebo and renal function was measured. As shown in FIG. 20, inhibition of TLR4 in these mice was associated with significant reduction in creatinine indicating that TLR4 antagonism is a treatment for the renal dysfunction of cirrhosis.

Example 6: Administration of TLR4 Antagonists in Animals with Paracetamol Overdose In animals with paracetamol overdose, which is known to cause renal failure independent of the severity of liver failure, the TLR4 antagonist STM 28 was found to prevent renal failure. Normal mice were treated with 400 mg of paracetamol intra-peritoneally with or without the TLR4 antagonist STM28. FIG. 21 shows that the animals treated with STM28 were protected from the renal dysfunction that was induced directly by paracetamol indicating that TLR 4 antagonism may be protective directly against the renal tubular damage induced by paracetamol.

Example 7: Increased TLR4 Expression in the Brain of Cirrhotic Animals

Figure 23:
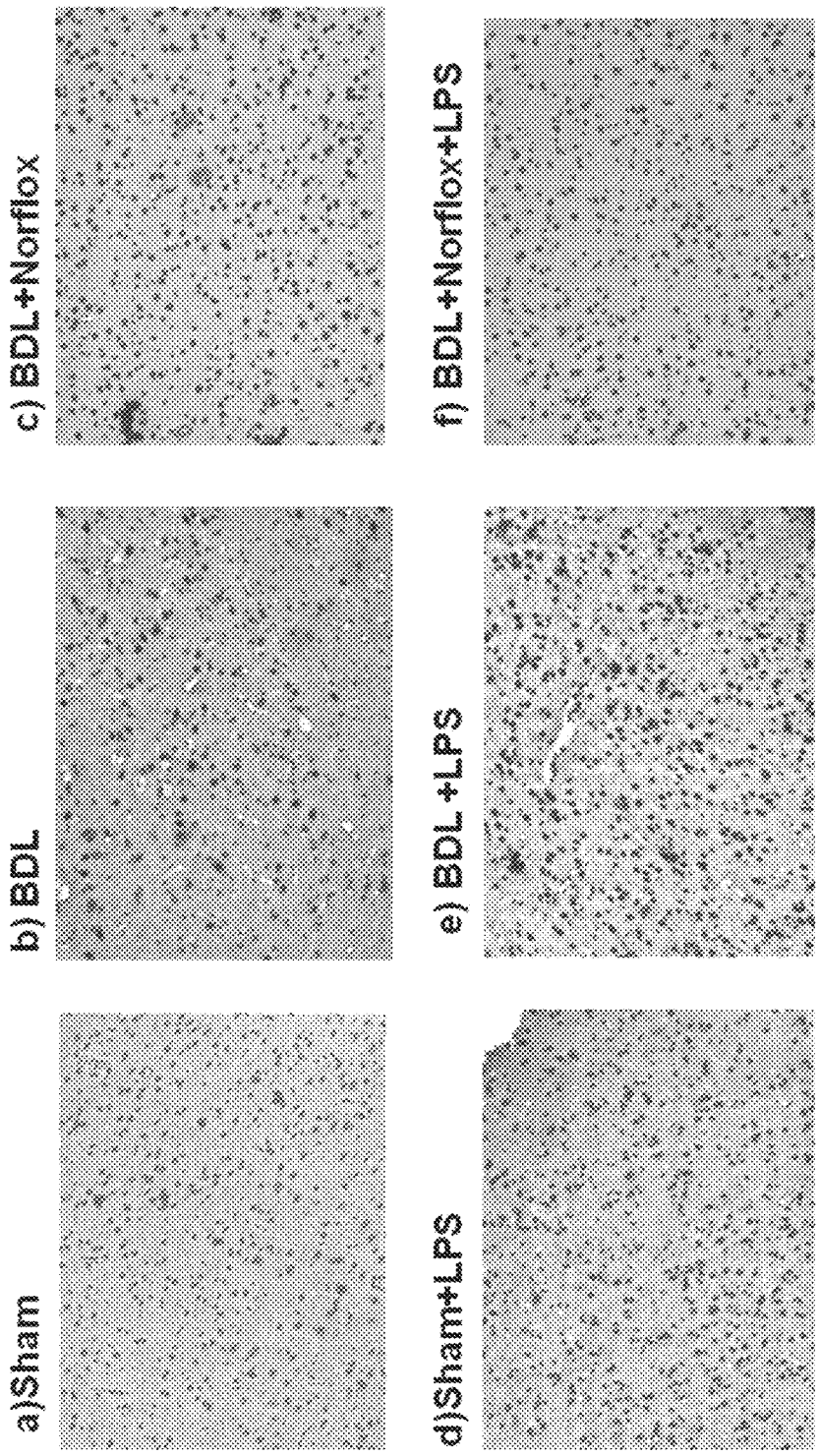
Figure 24:
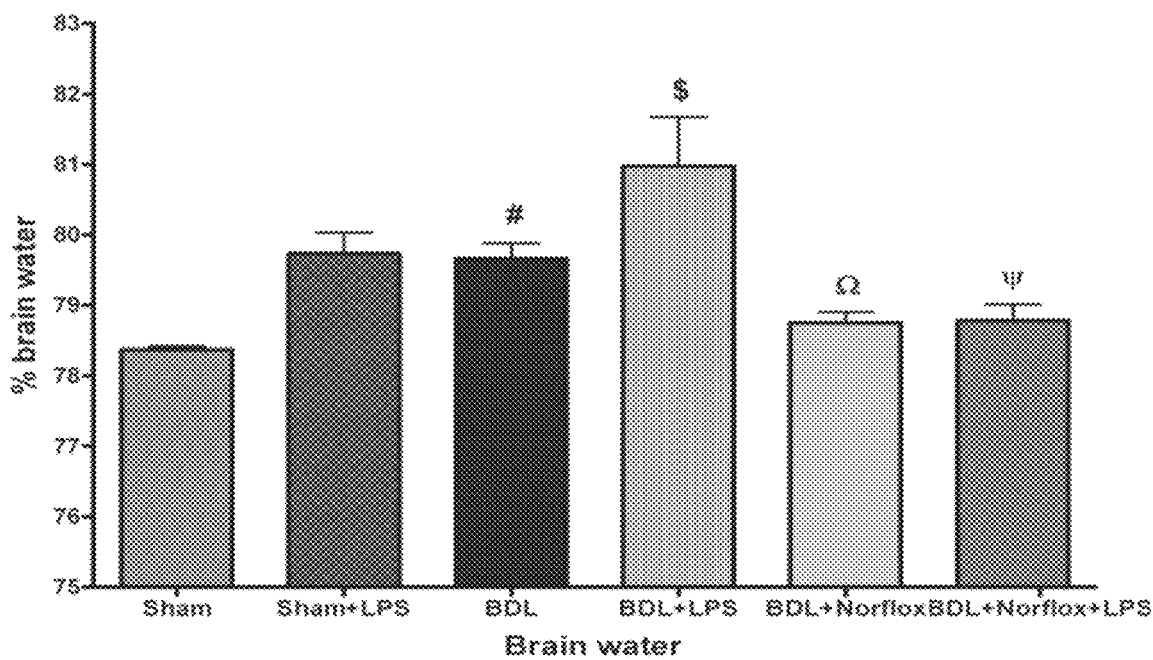
Figure 25:
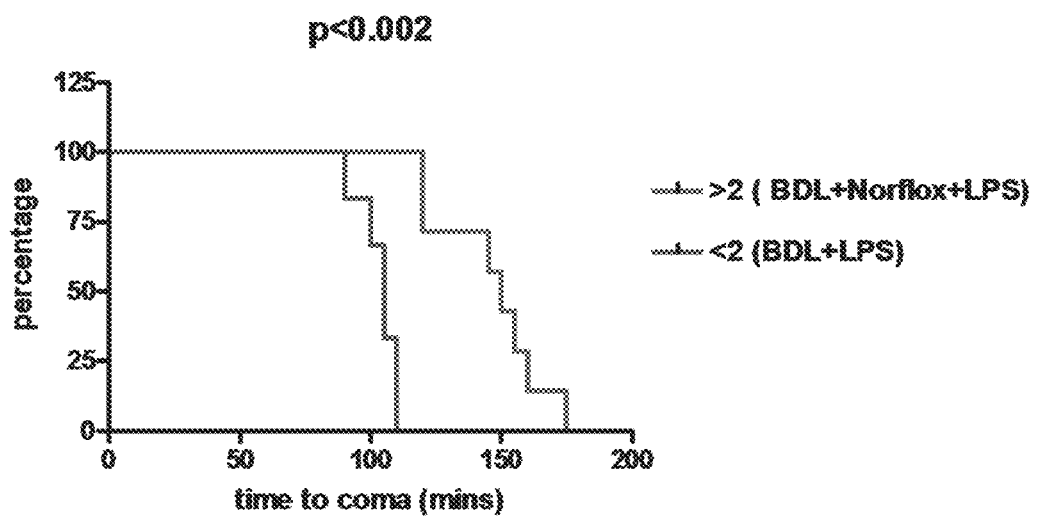

Experiments were carried out using Sham treated and BDL rats as described above. The animals were treated with LPS to mimic the effects of superimposed inflammation and/or Norfloxacin. As shown in FIG. 22, brain TLR4 expression was increased in the bile duct ligated (BDL) model of cirrhosis compared with Sham (normal) rats which was further increased when with superimposed inflammation (BDL+LPS). This increase could be prevented by gut decontamination with Norfloxacin. As shown in FIG. 23, TLR4 expression was increased in the BDL rats (C) compared with Sham (normal) (A) rats which was further increased when with superimposed inflammation (BDL+LPS) (D). This increase could be prevented in both the BDL animals (E) and also those treated with LPS (F) by gut decontamination with Norfloxacin. As shown in FIG. 24, brain water was increased in the BDL rats compared with Sham (normal) rats which was further increased when with superimposed inflammation (BDL+LPS). This increase in brain swelling measured by brain water could be prevented by gut decontamination with Norfloxacin. As shown in FIG. 25, reduction in TLR4 expression induced by administration of Norfloxacin (norflox) was associated with improvement in survival of BDL rats administered LPS (lipolysaccharide)

The invention claimed is:

1. A method for reducing plasma ammonia in a patient comprising administering to the patient an effective amount of an antagonist of TLR4, wherein the TLR4 antagonist comprises TAK-242 or STM28.

2. The method of claim 1, wherein the patient has been diagnosed with organ dysfunction.

3. The method of claim 1, wherein the patient has been diagnosed with dysfunction or swelling of the brain.

4. The method of claim 1, wherein the patient has been diagnosed with hyperammonemia.

5. The method of claim 1, wherein the TLR4 antagonist comprises STM28.

6. The method of claim 1, wherein the TLR4 antagonist comprises TAK-242.

7. A method of treating hyperammonemia in a patient comprising administering to said patient a therapeutically-effective amount of an antagonist of TLR4, wherein the TLR4 antagonist comprises TAK-242 or STM28.

8. The method of claim 7, wherein the patient has been diagnosed with organ dysfunction.

9. The method of claim 8, wherein the patient has been diagnosed with dysfunction or swelling of the brain.

10. The method of claim 7, wherein the patient has been diagnosed with hyperammonemia.

11. The method of claim 7, wherein the TLR4 antagonist comprises STM28.

12. The method of claim 7, wherein the TLR4 antagonist comprises TAK-242.

* * * * *